(12) United States Patent
Liu et al.

(10) Patent No.: US 8,791,081 B2
(45) Date of Patent: Jul. 29, 2014

(54) MGMT INHIBITOR COMBINATION FOR THE TREATMENT OF NEOPLASTIC DISORDERS

(75) Inventors: Lili Liu, Macedonia, OH (US); Stanton Gerson, Hunting Valley, OH (US)

(73) Assignee: Case Western Reserve University, Cleveland, OH (US)

( * ) Notice: Subject to any disclaimer, the term of this patent is extended or adjusted under 35 U.S.C. 154(b) by 593 days.

(21) Appl. No.: 12/529,643

(22) PCT Filed: Feb. 29, 2008

(86) PCT No.: PCT/US2008/055462
§ 371 (c)(1),
(2), (4) Date: Sep. 2, 2009

(87) PCT Pub. No.: WO2008/109417
PCT Pub. Date: Sep. 12, 2008

(65) Prior Publication Data
US 2010/0093647 A1    Apr. 15, 2010

Related U.S. Application Data

(63) Continuation-in-part of application No. 10/505,400, filed on Aug. 19, 2004, which is a continuation of application No. 10/079,049, filed on Feb. 19, 2002, now Pat. No. 6,635,677, which is a continuation-in-part of application No. 09/373,693, filed on Aug. 13, 1999, now Pat. No. 6,465,448.

(60) Provisional application No. 60/892,671, filed on Mar. 2, 2007.

(51) Int. Cl.
| | | |
|---|---|---|
| A61K 31/70 | (2006.01) |
| A61K 31/708 | (2006.01) |
| A61K 31/7064 | (2006.01) |
| A61K 31/7068 | (2006.01) |
| A61K 31/337 | (2006.01) |
| A61K 31/335 | (2006.01) |
| A61K 31/522 | (2006.01) |
| A61K 31/505 | (2006.01) |
| A61P 35/00 | (2006.01) |

(52) U.S. Cl.
USPC .......... 514/43; 514/45; 514/49; 514/23; 514/263.3; 514/449; 514/256; 514/171; 536/28.1

(58) Field of Classification Search
USPC .......... 514/43, 45, 49, 23, 263.3, 449, 256, 514/171; 536/28.1
See application file for complete search history.

(56) References Cited

U.S. PATENT DOCUMENTS 5,821,363 A * 10/1998 Wicnienski et al. .......... 548/215
6,777,415 B2    8/2004 Daley
2004/0053882 A1    3/2004 Smith et al.

OTHER PUBLICATIONS

Turriziani et al. (Pharmacological Research (2006) 53(4), 317-323) (Abstract ).*
Liu et al.; CN 1846686, Nov. 18, 2006 (Abstract sent).*
STN Abstract: Accession No. 2006:366015 Caplus; Document No. 145:327786; Title:O6- (4-Bromothenyl) guanine (PaTrin-2), a novel inhibitor of O6-alkylguanine DNA alkyl-transferase, increases the inhibitory activity of tremozolomide against human acute leukemia cells in vitro; Author; Turriziani et al., Pharmacological Research (2006), 53 (4), 317-323.

* cited by examiner

*Primary Examiner* — Shaojia Anna Jiang
*Assistant Examiner* — Michael C Henry
(74) *Attorney, Agent, or Firm* — Tarolli, Sundheim Covell & Tummino LLP

(57) ABSTRACT

A method of treating a neoplastic disease in a subject includes administering to neoplastic cells of the subject an MGMT inhibitor and at least one of an antimitotic agent or a DNA damaging agent.

8 Claims, 16 Drawing Sheets

A

B

C

D

MGMT INHIBITOR COMBINATION FOR THE TREATMENT OF NEOPLASTIC DISORDERS

RELATED APPLICATION

This application corresponds to PCT/US08/055462, filed Feb. 29, 2009 which claims priority from U.S. Provisional Application No. 60/892,671, filed Mar. 2, 2007, and is a continuation-in part of U.S. patent application Ser. No. 10/505,400, filed Aug. 19, 2004, which is a continuation of application Ser. No. 10/079,049, filed Feb. 19, 2002, now U.S. Pat. No. 6,635,677, which is a continuation-in-part of application Ser. No. 09/373,693, filed Aug. 13, 1999, now U.S. Pat. No. 6,465,448, which are incorporated herein by reference in their entirety.

GOVERNMENT FUNDING

This invention was made with government support under Grant Nos. NIH CA-82292, and NIH-CA-086357 awarded by the National Institutes of Health. The government has certain rights in the invention.

BACKGROUND OF THE INVENTION

Cancer continues to be a worldwide problem. The American Cancer Society estimates that more than 1,500 people will die of cancer each day in the United States alone in 2007. Finding novel compositions and methods for the treatment of cancer is of vital interest. The treatment of cancer falls into three general categories: chemotherapy, radiation therapy and surgery. Often, therapies are combined since a combination of therapies often increases the probability the cancer will be eradicated as compared to treatment strategies utilizing a single therapy. Most typically, the surgical excision of large tumor masses is followed by chemotherapy and/or radiation.

Chemotherapeutic agents can work in a number of ways. For example, chemotherapeutics can work by interfering with cell cycle progression or by generating DNA strand breaks. If the cancer cell is not able to overcome the cell cycle blockage or cell injury caused by the therapeutic compound, the cell will often die via apoptotic mechanisms. The use of a single chemotherapeutic agent in the treatment of cancer, with or without surgery or radiation, has several disadvantages. First, the cells may develop resistance to the chemotherapeutic agent. Such resistance results either in the requirement for higher dosages of the drug and/or the renewed spread of the cancer. Chemotherapeutic agents can be toxic to the patient. Therefore, there is a practical upper limit to the amount that a patient can receive. However, if two chemotherapeutic agents are used in concert, the dosage of any single drug may be lowered. This is beneficial to the patient since using lower levels of chemotherapeutic agents is generally safer for the patient. Additionally, cancer cells are less likely to generate resistance to the combination of drugs as they are to a single drug.

The design of drug combinations for the chemotherapeutic treatment of cancer should be approached with the goals of 1) finding a combination that is synergistic with and not merely additive to the first compound with respect to the elimination of the tumor, and 2) finding a second drug that does not potentiate the toxic effects of the first chemotherapeutic agent. These conditions require a great deal of empirical testing of agents known to have anticancer properties with agents that either may have anticancer properties, or that may augment the first agent in other ways.

Cancers develop as a result of multiple somatic mutations in proto-oncogenes and tumor suppressor genes. O6-Methylguanine-DNA-methyltransferase (MGMT) has been well known as a DNA repair protein and protects cells against the somatic mutations frequently observed in various human neoplasms, e.g. G:C→A:T transitions found in the TP53 tumor suppressor gene. It is well established that O6-methylguanine is a carcinogenic DNA lesion formed by methylating agents. MGMT removes methyl and some other alkyl groups from the O6-methylguanine and has been shown to be important in resistance to alkylating therapeutic agents.

Therefore, what is needed are therapies that reduce myelosuppresion while utilizing the synergistic properties of two or more therapeutic agents for the treatment of cancer that have a broader range of targets or a different range of targets than those combination therapies already known.

SUMMARY OF THE INVENTION

The present invention relates to compositions and methods useful in the treatment of certain neoplastic disorders (e.g., cancer and solid tumors). In part, this application is based on the recognition that certain molecules that inhibit O6-Methylguanine-DNA-methyltransferase (MGMT) induce, augment, or potentiate mitotic death and the chemotherapeutic efficacy of certain antimitotic agents and DNA damaging agents.

One aspect of the invention relates to compositions and methods of treating neoplastic disorders, such as cancer and solid tumors, in a subject. In the method, an antimitotic agent and a MGMT inhibitor can be administered to neoplastic cells of the subject. The MGMT inhibitor can be administered at an amount effective to potentiate or enhance the effect of the antimitotic agents at promoting mitotic cell death, with typical features of mitotic catastrophe, including G2/M arrest, disturbed mitotic progression, abnormal mitosis, and/or apoptosis of the neoplastic cells.

The antimitotic agents can comprise any agent that prevents or inhibits cellular mitosis and/or cellular growth by inhibiting cellular division. The antimitotic agents, can comprise, for example, microtubule modulators, such a taxane (e.g., taxol, paclitaxel, taxotere, docetaxel), podophyllotoxins, and vinca alkaloids (e.g., vincristine, vinblastine, vindesine, vinorelbine), colchicine, dolastatin, and nocodazole. In another aspect, the taxane has the following general structure:

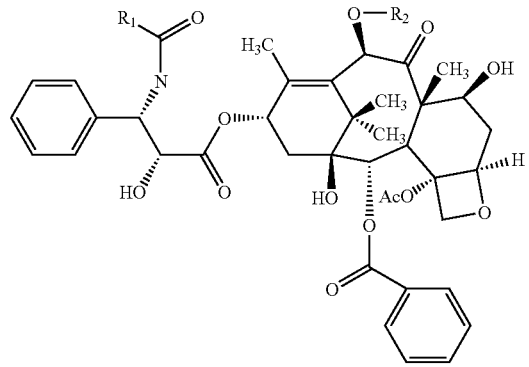

where $R_1$ is $C_6H_5$ or $(CH_3)_3C-O$ and $R_2$ is Ac or H.

The MGMT inhibitor can include, fore example, an O6-substituted guanine derivative or a glucose conjugate thereof. In another aspect of the invention, the O6-substituted guanine derivative can be O6-benzylguanine (BG), O6-2-fluoropyridinylmethyl guanine (FPG), O6-3-iodobenzyl guanine, O6-4-bromophenylguanine (PaTrin-2, UK), and O6-5-iodothenylguanine, O6-benzyl-8-oxoguanine (MW 257), O6-(p-chlorobenzyl)guanine, O6-(p-methylbenzyl)guanine (MW255), O6-(p-bromobenzyl)guanine (MW 320), O6-(p-isopropylbenzyl)guanine (MW 283), O6-(3,5-dimethylbenzyl)guanine (MW 269), O6-(p-n-butylbenzyl)guanine (MW 297), O6-(p-hydroxymethybenzyl)guanine (MW271), O6-benzylhypoxanthine, N2-acetyl-O6-benzylguanine (MW 283), N2-acetyl-O6-benzyl-8-oxo-guanine (MW 299), 2-amino-6-(p-methyl-benzyl-thio)purine, 2-amino-6-(benzyloxy)-9-[(ethoxycarbonyl)methyl]purine, 2-amino-6-(benzyloxy)-9-(pivaloyloxymethyl)purine, 2-amino-6-(benzyl-thio)purine, O6-benzyl-7,8-dihydro-8-oxoguanine (8-oxo-BG), 2,4,5-triamino-6-benzyloxyprimidine (5-amino-BP), O6-benzyl-9-[(3-oxo-5α-androstan-17β-yloxycarbonyl)methyl]guanine (DHT-BG), O6-benzyl-9-[(3-oxo-4-androsten-17β-yloxycarbonyl)methyl(guanine (AND-BG), and 8-amino-O6-benzylguanine (8-amino-BG) as well as C8-linker-glucose-conjugates thereof and combinations thereof.

In other aspects of the invention, MGMT inhibitor can be a pyrimidine compounds such as 2,4-diamino-6 benzyloxy-5-nitrosopyrimidine (5-nitroso-BP) and 2,4-diamino-6-benzyloxy-5-nitropyrimidine (5-nitro-BP), and/or 2-amino-4-benzyloxy-5-nitropyrimidine as well as combinations thereof and combinations with the foregoing O6-substituted guanine derivatives.

The formulations and compositions disclosed herein may be useful in the treatment of neoplastic disorders, such as cancers, carcinomas, melanomas, sarcomas, lymphomas, leukemias, astrocytomas, gliomas, malignant melanomas, chronic lymphocytic leukemia, lung cancers, and breast cancers and solid tumors.

In yet another embodiment, the application provides kits comprising:

1) a first pharmaceutical preparation comprising an antimitotic agent; and 2) a second pharmaceutical preparation comprising an MGMT inhibitor, and instructions for administering the first and second pharmaceutical preparations to a patient for the treatment of the neoplastic disorder.

In certain embodiments, the invention contemplates that antimitotic agents, such as taxol, paclitaxel, taxotere, docetaxel, may be used together with MGMT inhibitors, such as O6-benzylguanine (BG), O6-2-fluoropyridinylmethyl guanine (FPG), O6-3-iodobenzyl guanine, O6-4-bromophenylguanine (PaTrin-2, UK), and O6-5-iodothenylguanine, O6-benzyl-8-oxoguanine (MW 257), O6-(p-chlorobenzyl) guanine, O6-(p-methylbenzyl)guanine (MW255), O6-(p-bromobenzyl)guanine (MW 320), O6-(p-isopropylbenzyl) guanine (MW 283), O6-(3,5-dimethylbenzyl)guanine (MW 269), O6-(p-n-butylbenzyl)guanine (MW 297), O6-(p-hydroxymethybenzyl)guanine (MW271), O6-benzylhypoxanthine, N2-acetyl-O6-benzylguanine (MW 283), N2-acetyl-O6-benzyl-8-oxo-guanine (MW 299), 2-amino-6-(p-methyl-benzyl-thio)purine, 2-amino-6-(benzyloxy)-9-[(ethoxycarbonyl)methyl]purine, 2-amino-6-(benzyloxy)-9-(pivaloyloxymethyl)purine, 2-amino-6-(benzyl-thio)purine, O6-benzyl-7,8-dihydro-8-oxoguanine (8-oxo-BG), 2,4,5-triamino-6-benzyloxyprimidine (5-amino-BP), O6-benzyl-9-[(3-oxo-5α-androstan-17β-yloxycarbonyl)methyl]guanine (DHT-BG), O6-benzyl-9-[(3-oxo-4-androsten-17β-yloxycarbonyl)methyl(guanine (AND-BG), 8-amino-O6-benzylguanine (8-amino-BG), C8-linker-glucose-conjugates thereof, 2,4-diamino-6 benzyloxy-5-nitrosopyrimidine (5-nitroso-BP) and 2,4-diamino-6-benzyloxy-5-nitropyrimidine (5-nitro-BP), 2-amino-4-benzyloxy-5-nitropyrimidine, and combinations thereof.

The present invention is not limited by the order in which the MGMT inhibitor and the antimitotic agent are administered. In one embodiment, the MGMT inhibitor and the antimitotic agent are administered sequentially. In another embodiment, the MGMT inhibitor and the antimitotic agent are administered as a combined formulation (e.g., a formulation comprising taxol and O6-benzylguanine (BG)).

The present invention is not limited to the method of administration of the treatment. In one embodiment, the treatment is administered orally. In another embodiment the treatment is administered intravenously. In yet another embodiment, the treatment is administered intraperitoneally. In yet another embodiment, the treatment is administered directly to a tumor by injection or, in the case of skin tumors, for example, by direct application of creams or ointments. In certain embodiments, one agent is administered by one route, while the second agent is administered by a second route.

Another aspect of the invention relates to compositions and method of treating neoplastic disorders by administering to neoplastic cells of a subject a DNA damaging agent in conjunction with an MGMT inhibitor and optionally an antimitotic agent. It is believed that inaction of MGMT by the MGMT inhibitor in the presence of DNA damage caused by a DNA damaging agent in accordance with the present invention can initiate mitotic catastrophe and/or potentiate apoptotic cell death through interruption of DNA mitotic progression. When administered with both a DNA damaging and an antimitotic agent, the MGMT inhibitor can enhance the cytotoxic effect of each agent on the neoplastic cells by enhancing both mitotic catastrophe and apoptosis.

In one aspect of the invention, the DNA damaging agent that is administered in conjunction with the MGMT inhibitor and potentially the antimitotic agent can comprise an alkylating agent, such as a nitrogen mustard (e.g., chlorambucil, chlormethine, cyclophosphamide, ifosfamide, and melphalan) (and related purine analogs), fludarabine, bendamustine hydrochloride, a nitrososureas (e.g., carmustine, fotemustine, lomustine, streptozocin), a platinum complex (e.g., carboplatin, cisplatin, oxaliplatin, and BBR3464), busulfan, dacarbazine, mechlorethamine, procarbazine, temozolomide, thiotepa, uramustine, and combinations thereof.

In another aspect of the invention, the DNA damaging agent can comprise ionizing radiation such as X-ray radiation, gamma radiation, UVA, and UVB, that can be administered to subject at dosage effective to cause DNA damage. Techniques for administering the ionizing radiation to the subject can include radiotherapy techniques such as external beam radiotherapy, teletherapy, brachytherapy, sealed source radiotherapy, and unsealed source radiotherapy. It will be appreciated that the ionizing radiotherapy can be administered as the sole DNA damaging agent or in conjunction with other DNA damaging agents and the antimitotic agent.

In an aspect of the invention, the MGMT inhibitor, the DNA damaging agent and, potentially, the antimitotic agent can be administered sequentially. In another aspect, the MGMT inhibitor, the DNA damaging agent, and potentially the antimitotic agent can be administered at the same time, for example as a combined formulation (e.g., a formulation comprising taxol, O6-benzylguanine (BG), and cisplatin).

DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Definitions

Figure 1:
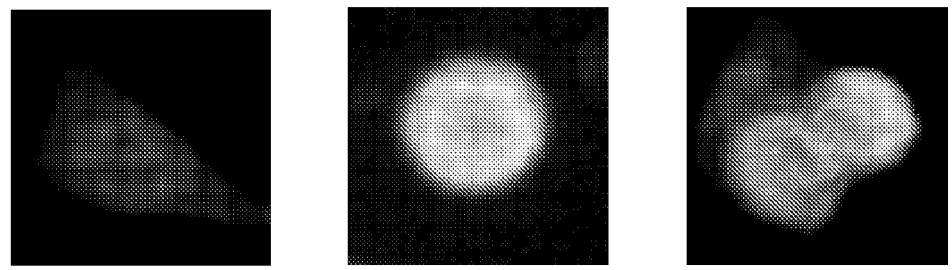
FIG. 1 illustrates (A). Dual staining with MPM2 and pH3 in mitotic cells. (B). Phosphorylation of MGMT in mitotic cells. (C). MGMT is co-IP with MPM2. (D) MGMT (green) is highly expressed in mitotic cells and colocalized with MPM2 (red).
Figure 1:
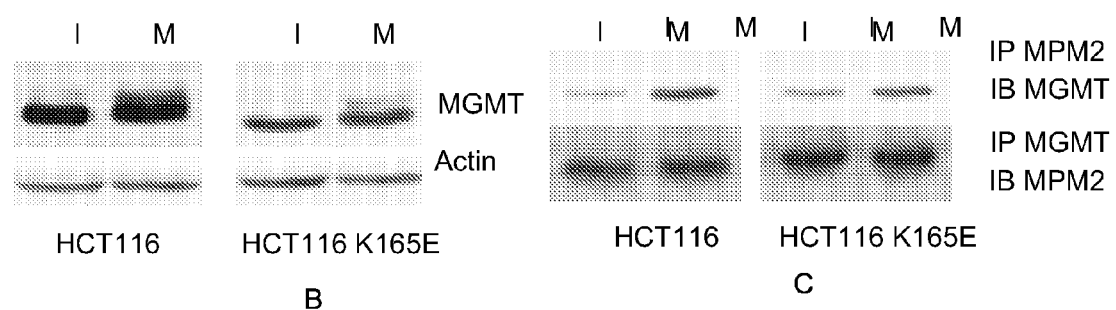
Figure 1:
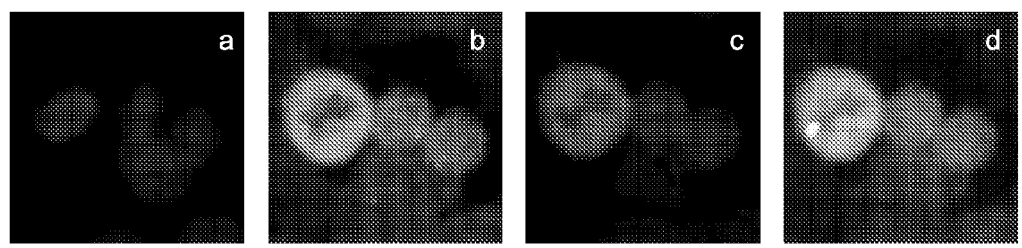

To facilitate understanding of the invention, a number of terms are defined below.

As used herein "agent" or "drug" is used to denote a chemical compound, a mixture of chemical compounds, a biological macromolecule, or an extract made from biological materials such as bacteria, plants, fungi, or animal (particularly mammalian) cells or tissues that are suspected of having therapeutic properties. The agent or drug may be purified or partially purified.

As used herein "subject" is used to denote a human or other animal, such as farm animals or laboratory animals (e.g., guinea pig or mice) capable of having neoplastic diseases, either naturally occurring or induced, including but not limited to cancer.

As used herein "neoplastic disease" or "neoplastic disorder" is used to denote those diseases, which form an abnormal, disorganized growth in a tissue or organ, usually forming a distinct mass. Such a growth is called a neoplasm, and is also known as a tumor or cancer.

As used herein "mitotic death" is used to denote cell death occurring during or resulting from mitosis. Mitotic death can result from a combination of deficient cell-cycle checkpoints, in particular the DNA structure checkpoints and the spindle assembly checkpoint, and cellular damage.

The present invention relates to formulations and methods useful in the treatment of certain neoplastic disorders (e.g., cancer and solid tumors). In part, this application is based on the recognition that certain molecules that inhibit O6-Methylguanine-DNA-methyltransferase (MGMT) induce, augment, or potentiate mitotic death and the chemotherapeutic efficacy of certain antimitotic agents and DNA damaging agents.

Cell division is controlled by the regulation of mitotic progression. The anti-tumor or anti-cancer effect of antimitotic agents can therefore be enhanced through the disturbance of mitotic progression and induction of mitotic death. Thus, it has been found that MGMT inhibitors, such as O6-guanine derivatives, are useful as an inhibitor of the mitotic progression. Inactivation of MGMT promotes mitotic catastrophe in target cells after treatment with antimitotic agents and/or DNA damaging agents. The inventors have shown that inactivation of MGMT promotes mitotic death with the typical features of mitotic catastrophe, including prolonged G2/M arrest, disturbed mitotic progression, abnormal mitosis including multiple spindles, multinucleated giant cells, and an aneuploid phenotype.

The present invention provides compositions and methods for the treatment of neoplastic disorders, such as cancer and solid tumors that use an antimitotic agent and/or DNA damaging agents. Antimitotic agents are commonly used to treat cancers, as they are known to inhibit cell growth by stopping cell division. Antimitotic agents are also commonly referred to as antimicrotubule agents and mitotic inhibitors.

In a certain aspect of the invention, the antimitotic agent is a taxane. Taxanes have been used to produce various chemotherapy drugs. The taxanes are diterpenes produced by the plants of the genus Taxus (yews). They were first derived from natural sources, but others have been synthesized artificially.

The principal mechanism of the taxane class of drugs is the inhibition of microtubule function, which is essential to cell division. Taxanes stabilize GDP-bound tubulin in the microtubule. This causes microtubules to arrange themselves in a parallel array rather than the required arrangement of the mitotic spindle leading to mitotic arrest. Taxanes are highly lipophilic, as they do not form stable salts with acids or bases, and are insoluble in water. Intravenous taxane infusion, for example, is commonly prepared as a nonaqueous solution in polyoxyethylated castor oil and dehydrated alcohol.

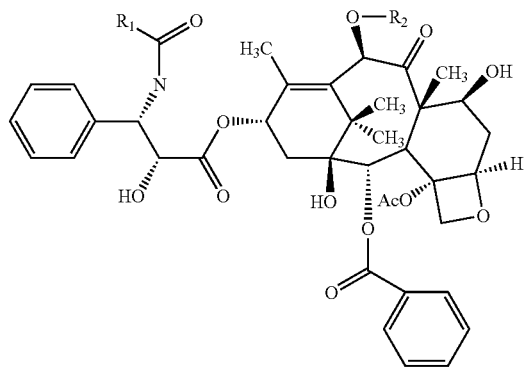

In an aspect of the invention, the taxane has the following general structure:

where $R_1$ is $C_6H_5$ or $(CH_3)_3C$—O and $R_2$ is Ac or H. Examples of taxanes with this formula include paclitaxel, and docetaxel.

Docetaxel is semi-synthetic analogue of paclitaxel differing in structure from paclitaxel in having one less acetate group and tertiary butyl carbamate functionality in place of the benzoamido group. Docetaxel is a clinically well-established anti-neoplastic medication used mainly for the treatment of breast, ovarian, and non-small cell lung cancer (Lyseng-Williamson et al. 2005). The injectable formulation, consisting of docetaxel in polysorbate 80, is commonly diluted prior to use.

Other example of antimitotic agents can include podophyllotoxins, and vinca alkaloids (e.g., vincristine, vinblastine, vindesine, vinorelbine), colchicine, dolastatin, and nocodazole In one aspect of the invention, a method is provided for enhancing the therapeutic effect of an antimitotic agent, such as a taxane, by administering a MGMT inhibitor. The MGMT inhibitor can be administered at an amount effective to potentiate or enhance the effect of the antimitotic agents at promoting mitotic cell death, with typical features of mitotic catastrophe, including G2/M arrest, disturbed mitotic progression, abnormal mitosis, and/or apoptosis of the neoplastic cells. The MGMT inhibitor may be administered either prior to the administration of the anticancer agent or at the same time. It may be administered either orally or intravenously.

In certain aspects, the MGMT inhibitor can be an O6-substituted guanine derivative or a glucose conjugate thereof. In another aspect of the invention, the O6-substituted guanine derivative can be O6-benzylguanine (BG), O6-2-fluoropyridinylmethyl guanine (FPG), O6-3-iodobenzyl guanine, O6-4-bromophenylguanine (PaTrin-2, UK), and O6-5-iodothenylguanine, O6-benzyl-8-oxoguanine (MW 257), O6-(p-chlorobenzyl)guanine, O6-(p-methylbenzyl)guanine (MW255), O6-(p-bromobenzyl)guanine (MW 320), O6-(p-isopropylbenzyl)guanine (MW 283), O6-(3,5-dimethylbenzyl)guanine (MW 269), O6-(p-n-butylbenzyl)guanine (MW 297), O6-(p-hydroxymethybenzyl)guanine (MW271), O6-benzylhypoxanthine, N2-acetyl-O6-benzylguanine (MW 283), N2-acetyl-O6-benzyl-8-oxoguanine (MW 299), 2-amino-6-(p-methyl-benzyl-thio)purine, 2-amino-6-(benzyloxy)-9-[(ethoxycarbonyl)methyl]purine, 2-amino-6-(benzyloxy)-9-(pivaloyloxymethyl)purine, 2-amino-6-(benzyl-thio)purine, O6-benzyl-7,8-dihydro-8-oxoguanine (8-oxo-BG), 2,4,5-triamino-6-benzyloxyprimidine (5-amino-BP), O6-benzyl-9-[(3-oxo-5α-androstan-17β-yloxycarbonyl)methyl]guanine (DHT-BG), O6-benzyl-9-[(3-oxo-4-androsten-17β-yloxycarbonyl)methyl(guanine (AND-BG), and. 8-amino-O6-benzylguanine (8-amino-BG) as well as C8-linker-glucose-conjugates thereof and combinations thereof.

In other aspects of the invention, MGMT inhibitor can be a pyrimidine compounds such as 2,4-diamino-6 benzyloxy-5-nitrosopyrimidine (5-nitroso-BP) and 2,4-diamino-6-benzyloxy-5-nitropyrimidine (5-nitro-BP), and/or 2-amino-4-benzyloxy-5-nitropyrimidine as well as combinations thereof and combinations with the foregoing O6-substituted guanine derivatives.

In a specific aspect of the invention, the MGMT inhibitor can comprise O6-Benzylguanine (BG). O6-Benzylguanine (BG) is a direct substrate of MGMT that rapidly depletes MGMT in mammalian cells. BG has been used previously to sensitize a variety of cancer cells and tumor xenografts to the alkylating agent BCNU (Dolan et al., 1990, 1991, 1993; Mitchell et al., 1992; Baer et al., 1993; Felker et al., 1993; Gerson et al., 1993; Magull-Seltenreich and Zeller, 1995; Wedge and Newlands, 1996; Kurpad et al., 1997; Phillips et al., 1997). BG alone has been well tolerated in mice and rats (Chinnasamy et al., 1997; Kurpad et al., 1997). The efficacy of BG as a chemomodulator also depends on the extent of MGMT depletion in normal tissues, and the optimal therapeutic index for a combination BG and antimitotic agent therapy can achieved by depleting MGMT in a target tumor for a suitable amount of time with minimal depletion in normal tissues.

The formulations and compositions disclosed herein may be useful in the treatment of neoplastic disorders, such as cancers, carcinomas, melanomas, sarcomas, lymphomas, leukemias, astrocytomas, gliomas, malignant melanomas, chronic lymphocytic leukemia, lung cancers, and breast cancers.

In yet another embodiment, the application provides kits comprising: 1) a first pharmaceutical preparation comprising an antimitotic agent; and 2) a second pharmaceutical preparation comprising an MGMT inhibitor, and instructions for administering the first and second pharmaceutical preparations to a patient for the treatment of a neoplastic disorder.

In certain embodiments, the invention contemplates that antimitotic agents, such as taxol, paclitaxel, taxotere, docetaxel, may be used together with MGMT inhibitors, such as O6-benzylguanine (BG), O2-fluoropyridinylmethyl guanine (FPG), O6-3-iodobenzyl guanine, O6-4-bromophenylguanine, and O6-5-iodothenylguanine, as a treatment for certain tumors that are resistant to treatment by the antimitotic agent alone.

With regard to the treatment of cancer, the present invention contemplates methods of treating cancer that utilize an antimitotic agent, such as taxol, paclitaxel, taxotere, docetaxel, in conjunction with an MGMT inhibitor that is capable of potentiating the toxic effect of the antimitotic agent with respect the cancer cells. More specifically, the invention relates to potentiating the effect of antimitotic agents, such as taxol, paclitaxel, taxotere, docetaxel, with agents that that promote mitotic cell death with typical features of mitotic catastrophe, including G2/M arrest, disturbed mitotic progression, abnormal mitosis.

The present invention is not limited by the order in which the agents are administered. In one embodiment, the agents are administered sequentially. In another embodiment, the agents are administered as a combined formulation (e.g., a formulation comprising taxol and O6-benzylguanine (BG)). In one embodiment, the present invention contemplates a method of treating cancer by administering to a patient diagnosed with cancer a first formulation comprising a MGMT inhibitor, such as O6-benzylguanine (BG), and a second formulation comprising an antimitotic agent, such as taxol.

The present invention is not limited to the method of administration of the treatment. In one embodiment, the antimitotic agent and the MGMT inhibitor can be administered orally. In another embodiment, the antimitotic agent and the MGMT inhibitor can be administered intravenously. In yet another embodiment, the antimitotic agent and the MGMT inhibitor can be administered intraperitoneally. In yet another embodiment, the antimitotic agent and the MGMT inhibitor can be administered directly to the tumor by injection or, in the case of skin tumors, for example, by direct application of creams or ointments. In certain embodiments, the antimitotic agent can be administered by one route, while the MGMT inhibitor can be administered by a second route.

Another aspect of the invention relates to compositions and method of treating neoplastic disorders by administering a DNA damaging agent in conjunction with an MGMT inhibitor and optionally an antimitotic agent. It is believed that inaction of MGMT by the MGMT inhibitor in the presence of DNA damage caused by a DNA damaging agent in accordance with the present invention can initiate mitotic catastrophe and potentially apoptotic cell death through interruption of DNA mitotic progression. When administered with both a DNA damaging and an antimitotic agent, the MGMT inhibitor can enhance the cytotoxic effect of each agent to neoplastic cells by enhancing both mitotic catastrophe and apoptosis.

In one aspect of the invention, the DNA damaging agent comprise an alkylating agent such as a nitrogen mustard (e.g., chlorambucil, chlormethine, cyclophosphamide, ifosfamide, and melphalan) (and related purine analogs), fludarabine, bendamustine hydrochloride, a nitrososureas (e.g., carmustine, fotemustine, lomustine, streptozocin), a platinum complex (e.g., carboplatin, cisplatin, oxaliplatin, and BBR3464), busulfan, dacarbazine, mechlorethamine, procarbazine, temozolomide, thiotepa, uramustine, and combinations thereof.

In another aspect of the invention, the DNA damaging agent can comprise ionizing radiation such as X-ray radiation, gamma radiation, UVA, and UVB that can be administered to subject at dosage effective to cause DNA damage. Techniques for administering the ionizing radiation to the subject can include radiotherapy techniques such as external beam radiotherapy, teletherapy, brachytherapy, sealed source radiotherapy, and unsealed source radiotherapy. It will be appreciated that the ionizing radiotherapy can be administered as the sole DNA damaging agent or in conjunction with other DNA damaging agents.

The MGMT inhibitor, the DNA damaging agent, and, potentially, the antimitotic agent can be administered sequentially. The MGMT inhibitor, the DNA damaging agent, and potentially the antimitotic agent can also be administered at the same time, for example as a combined formulation (e.g., a formulation comprising taxol, O6-benzylguanine (BG), and cisplatin).

EXAMPLE

MGMT has the Characteristics of a Mitotic Protein

To determine whether MGMT is regulated through the mitotic progression and how MGMT is associated with mitotic regulation, HCT116 and HCT116-K165E cells were treated with nocodazole (50 ng/ml for 16 hr) to arrest the majority of cells in the mitotic metaphase.

Mitotic cells were double stained with immunofluorescence by using two well know antibodies: a mitotic phosphoprotein monoclonal antibody (MPM2) to recognize mitotic phosphorylated proteins and an antibody to recognize phosphorylated histone H3 (pH3), a marker for mitotic cells.

As shown in FIG. 1, MPM2 and pH3 are specifically bound to mitotic cells.

Based on the fluorescent staining, a similar mitotic index (~80%) was scored in both MGMT wild type and K165E cell lines after a 16 hr-nocodazole treatment, indicating that point mutation occurred at 165 amino acid in MGMT gene does not alter mitotic progression in response to nocodazole.

The MGMT protein in cells arrested in mitotic phase by nocodazole (M) was compared with that in cells in interphase of cell cycle (I).

Notably, western blotting revealed that nocodazole treatment for 16 h altered the MGMT electrophoretical mobility pattern, resulting in two bands, one corresponding to the 23 kDa unphosphorylated MGMT and another to the slower mobility phosphorylated MGMT protein in both cell lines. MGMT was elevated and phosphorylated in mitotic cells (FIG. 1B) showing a mitosis associated-regulation pattern. MPM2 has been well documented to recognize more than 40 mitotic phosphoproteins, such as MAPK, HSP70, Cdc25 and DNA topoisomerase II$\alpha$ (Topo II $\alpha$) and the majority of these are phosphorylated on serine and threonine residue (>95%) followed by a proline. Thus, MPM2 has been well accepted as a useful tool to identify or to uncover a mitotic protein that is phosphorylated on Ser/Thr-Pro motifs. To determine whether MGMT protein is recognized by MPM2, mitotic and interphase cell lysates then were immunoprecipitated with MGMT or MPM2 antibodies and then co-immunoprecipitated MPM2 or MGMT was detected respectively by western blot analysis. Both wild type and K165E mutant MGMT immunoprecipitated from nocodazole-arrested mitotic cells were more strongly MPM2 reactive (FIG. 1C) compared to the immunoprecipitates from nonsynchronized cells. Dual immunofluorescence staining (FIG. 1D) revealed that the expression of MGMT (green) was increased in mitotic cells that were marked by MPM2 (red).

The colocalization of MGMT with MPM2 provides the evidence that MGMT protein and its phosphorylation status are regulated by the mitotic progression. K165E MGMT displayed a similar reaction with MPM2 in mitotic cells (data not shown).

Figure 2:
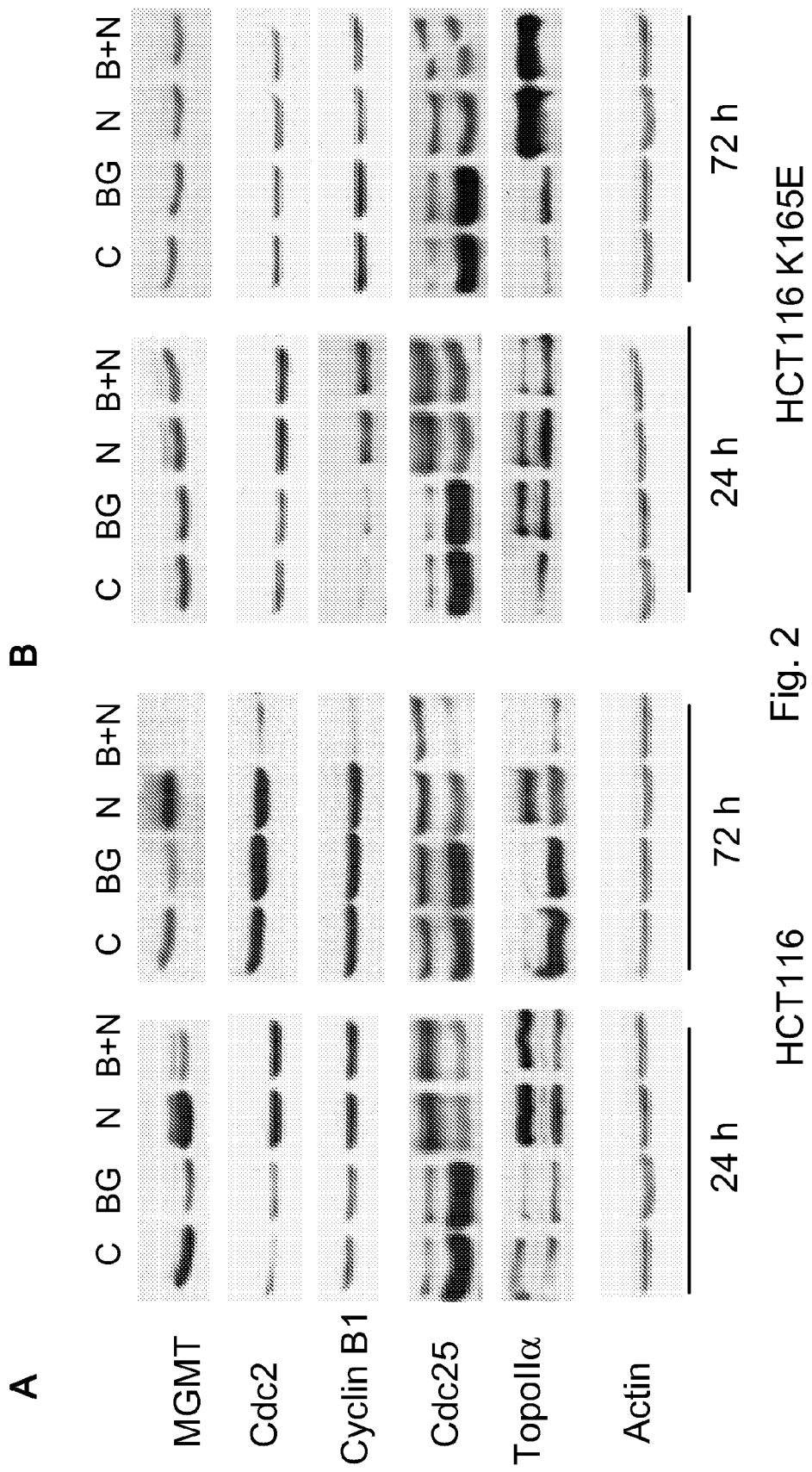
FIG. 2 illustrates a western blot in which MGMT and other mitotic proteins are down regulated concomitantly at 72 h after treatment with BG and Nocodazale in HCT116 but not in HCT116 K165E cells. C, Control, and N, nocodazole.

As expected, Cdc2/Cyclin B1, two crucial key components to drive the transition from G2 to M phase, were also noted to be transiently elevated at 24 hr exposure to nocodazole (FIG. 2).

The nature of relationship of MGMT with Cdc2/cyclinB1 during mitotic progression remains unclear, however, it appears to support the hypothesis that MGMT behaves like a mitotic component and may have a specific function in mitosis.

To investigate the molecular relationship of MGMT with other mitotic proteins in regulation of mitotic progression, we performed western blotting analysis in cells treated with nocodazole and BG together or separately, for 24 and 72 hr. As shown in FIG. 2, the kinetics of mitotic phosphorylation and dephosphorylation of MGMT concomitantly occurred with other mitotic phosphoproteins that are well known to be involved in regulation of mitotic progression such as Cdc25, showing increases in phosphorylation (up band) at 24 hr and dephosphorylation at 72 hr after nocodazole-treatment.

The most remarkable evidence was that a complete depletion of MGMT induced by BG plus noc at 72 hr was accompanied with the dramatic down-regulation of the all tested mitotic proteins (FIG. 2A). Treatment with BG alone displayed a decreased MGMT, apparently, BG alone has no effect on the expression of other mitotic proteins. In contrast, BG failed to deplete K165E MGMT and the levels of MGMT protein remained consistent in untreated and treated cells. Other mitotic proteins in cells treated with nocodazole alone or BG plus nocodazole at 72 hr displayed a similar pattern in HCT116 K165E cells (FIG. 2B). It seems obvious that loss of MGMT combined with a molecular event, in which mitotic progression is disrupted by nocodazole, has the impact on the stability or function of other mitotic proteins, leading to mitotic failure. Thus, how MGMT is involved in mitosis and how MGMT is related with these mitotic proteins during the mitotic progression seem necessary to be further studied.

Figure 3:
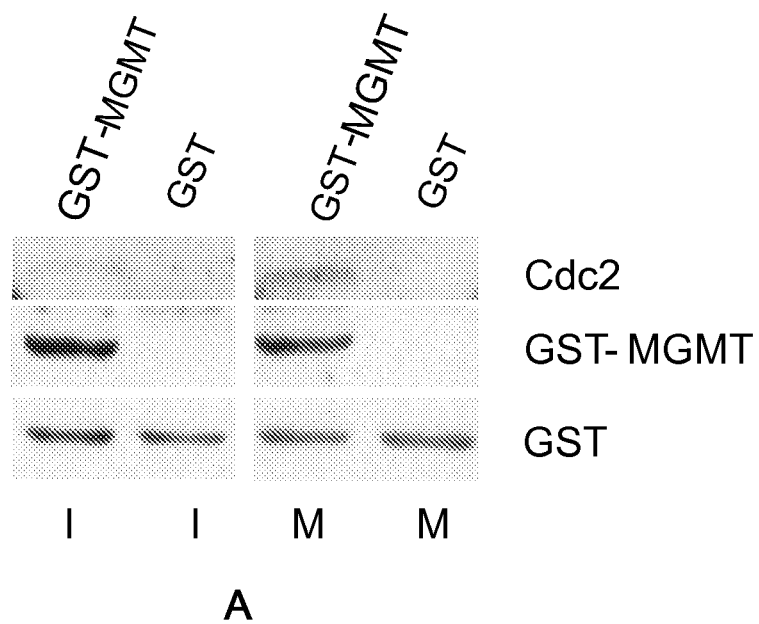
FIG. 3 illustrates (A). GST-pull down assay. (B) upper panel: co-immunostaining of MGMT with Cdc2 in mitotic cells lower panel: MGMT siRNA diminishes MGMT staining and Cdc2 co-staining signals in mitotic cells. I, interphase cell; M, mitotic cell.
Figure 3:
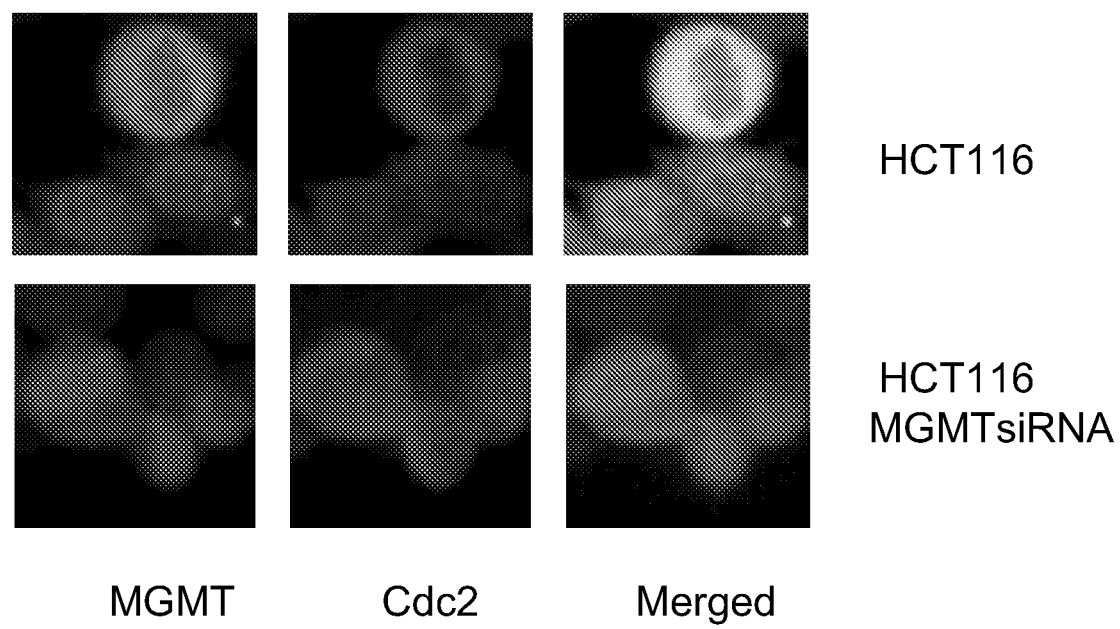

Mitotic events, including chromosome condensation, nuclear membrane breakdown and altered spindle dynamics, involve a series of mitotic proteins. Many of these are phosphorylated directly by mitotic kinase Cdc2 to regulate mitotic progression. To address the relationship between MGMT and Cdc2, GST pull down assays were performed. An in vitro MGMT-Cdc2 protein complex was detected in untreated (I: cells in interphase) and nocodazole (M: cells in mitotic phase) treated cells (FIG. 3A). The in vivo interaction was further confined by immunofluorescence studies. HCT116 cells stained for endogenous MGMT and Cdc2 displayed co-localization (FIG. 3B) and MGMT-siRNA diminished the co-staining of MGMT with Cdc2, suggesting that the interaction with Cdc2 may be one of the factors responsible for both the mitotic phosphorylation of MGMT and the regulatory mechanism of MGMT in the mitotic progression.

To further test whether MGMT plays a role in regulation of mitosis and inactivation of MGMT would disrupt mitotic progression and lead to mitotic catastrophe, we examined the relation of inactivated MGMT by BG with the cytotoxic effect of Taxol. Taxol binds microtubules and causes kinetic suppression of microtubule dynamics by enhancing their polymerization. In this way, it arrests cells at the metaphase-anaphase transition and subsequently leads to apoptotic death.

Fluorescence-immunostaining with phospho-histone H3 and MPM2 revealed that cells displayed increased abnormalities of mitotic features (FIG. 4C) after exposure to the combination of BG and taxol. In contrast, the treatment with taxol alone produced 2.8 and 39% of annexin V positive cells at 24 and 72 hr, respectively. BG alone had no effect on cell cycle arrest and prone-apoptotic activity in the absence of taxol treatment. The studies using the combination of BG and taxol help to rule out the concern that inactivation of MGMT by BG results in increase in DNA damage that affect cell cycle distribution and mitotic death. In taxol-treated cells, no DNA damage is a substrate for MGMT repair.

Figure 4:
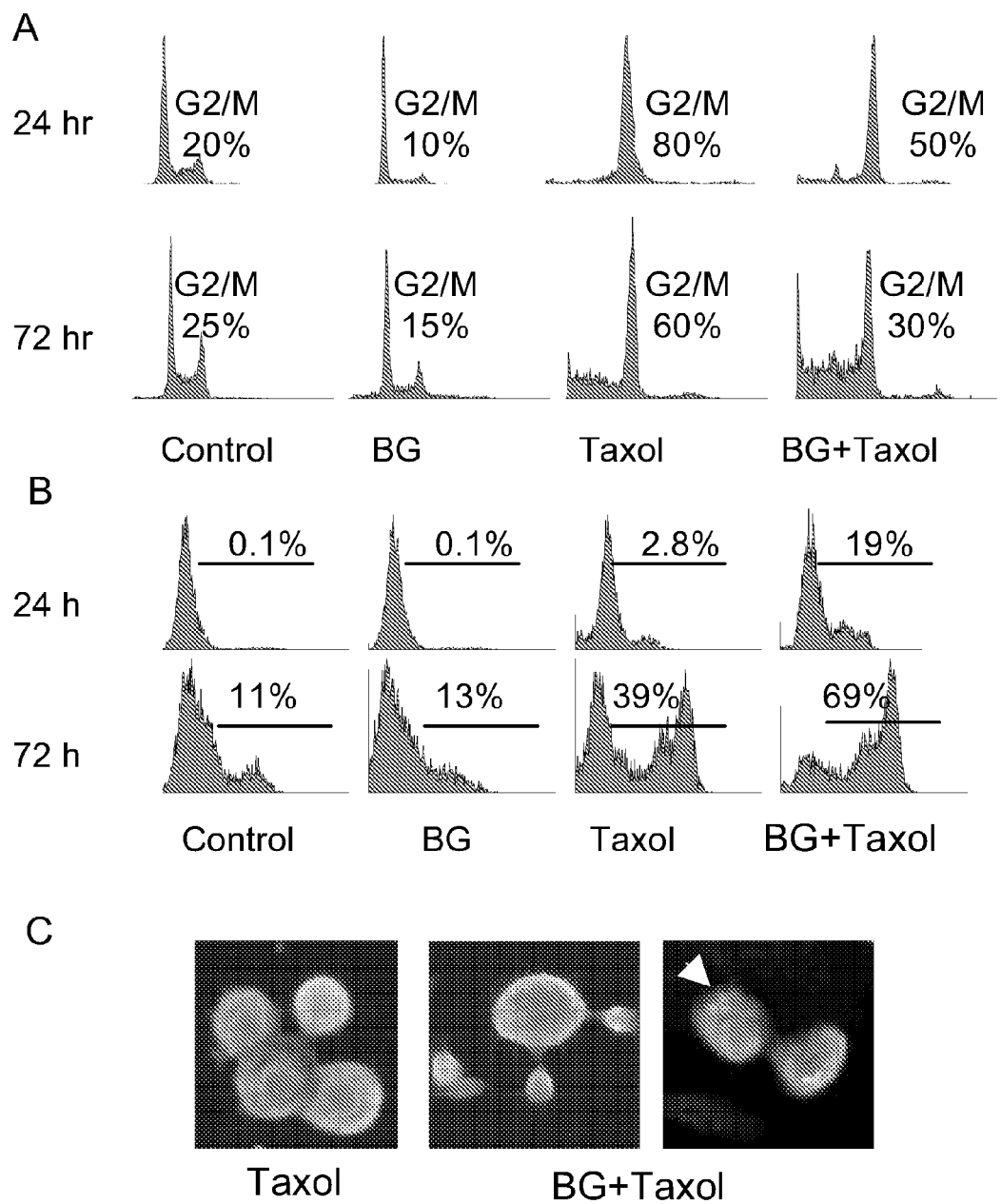
FIG. 4 illustrates the increase in mitotic abnormality and death by BG plus Taxol. (A) Cell cycle distribution. (B) Annexin staining. (C) Mitotic errors occur after treatment in BG plus Taxol. Arrow indicates unattached chromosomes.

Direct comparison between HCT116 cells at 24 and 72 hr after Taxol treatment with the presence or absence of BG by flow cytometric analysis. Cell cycle distribution revealed that dysfunctional MGMT resulted in a decrease in the percentage of cells arrested in Taxol-induced G2/M (FIG. 4A), suggesting the inhibition of mitotic entry after inactivation of MGMT by BG. A significant increase in apoptotic death was seen in the combination at 72 hr. As shown in FIG. 4B, the combination of BG and Taxol induced 19% of annexin V-positive cells at 24 hr. This was remarkably evident at 72 hr, 69% of the cells showed annexin V-positive, indicating that majority of mitotic cells die due to a failure of mitosis.

Figure 5:
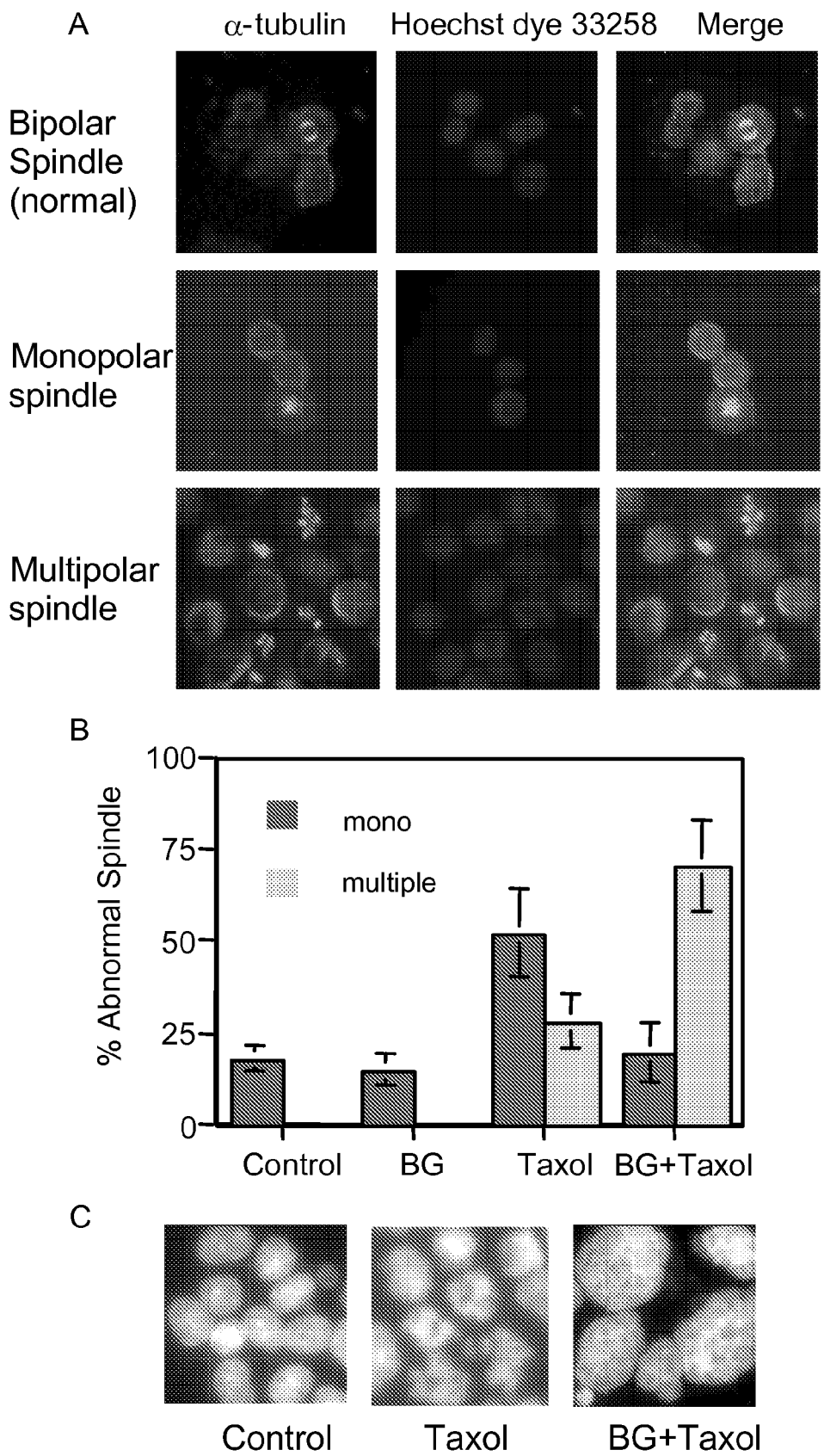
FIG. 5 illustrates inactivation of MGMT leads to increases in cell containing multipolar spindles and enlarged nuclear. (A) Mitotic spindles were labeled with tubulin (green) and DNA was stained with Hoechst dy 33258. (B) Quantitation of mitotic cells containing mono versus multipolar spindles 6 hr after drug treatments. (C) Enlargement of Nucleus in cells at 72 hr after treatment with BG and taxol.

To determine the mechanisms responsible for increased cell death after the treatment with BG plus taxol, HCT116 cells were stained with antibody to α-tubulin and mitotic cells (>300) were examined with immunofluorescence microscopy. One of the main consequences of the inactivation of MGMT was that over 70% mitotic cells display multipolar spindles (FIGS. 5A & B) after the combined treatment of BG (50 µM) with taxol (0.5 µM), which was 3-fold higher than that observed in cells treated with taxol only. The majority of abnormal spindles induced by taxol only were monopolar spindles, which were consistent with published data. Untreated or BG only treated cells containing monopolar spindle (lower than 20%) were also observed. It was apparent that majority of cells contain enlarged nucleus at 72 hr after treatment with BG and taxol compared to cells treated with taxol alone. This suggests that it is the result related to the inactivation of MGMT that induces multipolar spindles and the defects in cytokinesis. However, how is MGMT involved in these events that needs to be further studied.

Figure 6:
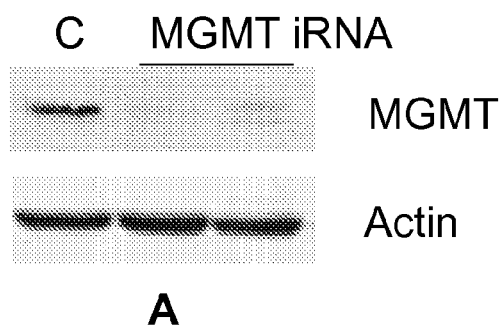
FIG. 6 illustrates (A) western blotting shows that level of MGMT protein is suppressed. (B) Suppression of MGMT by siRNA reduced mitotic death detected by Annexin V staining in cells treated with BG+taxol.
Figure 6:
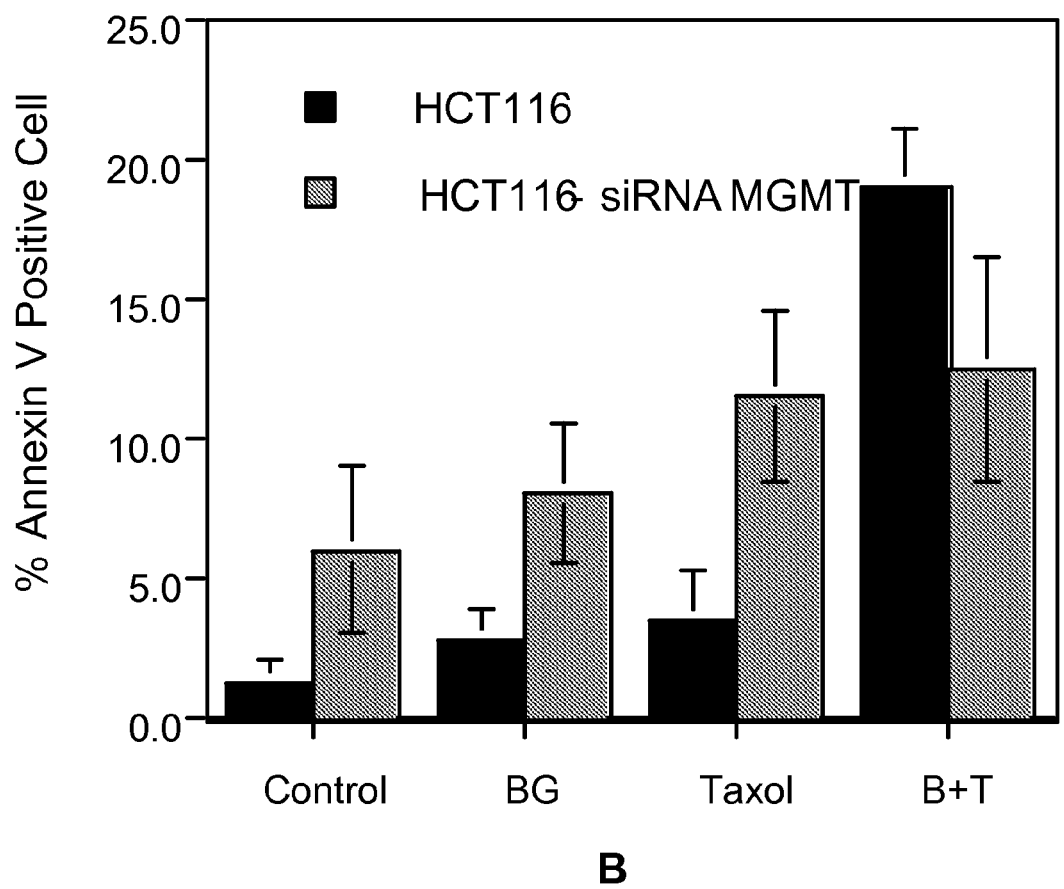

To further examine the role of inactivation of MGMT in promotion of mitotic death when cells are challenged with an agent that is able to induce mitotic perturbation, MGMT in HCT116 cells was knocked down using siRNA (FIG. 6A).

These cells were treated with taxol alone or BG plus taxol for 24 hrs and displayed a similar level of mitotic death detected using Annexin V staining (FIG. 6B). In contrast, in HCT116 cells, the combination of BG and taxol induced cell death was 4-fold higher than that in cells treated with taxol alone (FIG. 6B). These data indicate that mitotic death is associated with inactivation of MGMT.

Although the molecular mechanism of mitotic catastrophe is not clear yet, it is known that mitotic catastrophe is the response of mammalian cells to mitotic DNA damage and the defects in mitotic checkpoint.

Inactivation of MGMT Induced the Defect in Mitotic Checkpoint Become Prominent when Cells are Challenged with Mitotic or DNA Damage.

We have hypothesized although inactivation of MGMT may induce the defect in mitotic checkpoint, which may not harm cells in interphase but is lethal to the cells entering mitosis with the DNA damage. In our previous studies, we found that inactivation of MGMT induced abnormal mitosis was manifested when cells were insulted with DNA damaging agent, BCNU.

The effects of BCNU alone and BG plus BCNU were examined in relation to cell cycle arrest in HCT116 and HCT116 BBR (K165E) cells. Cell cycle analysis revealed that without treatment, there was no significant difference in the proportion of each cell cycle phase between HCT116 and HCT116 BBR (K165E).

Figure 7:
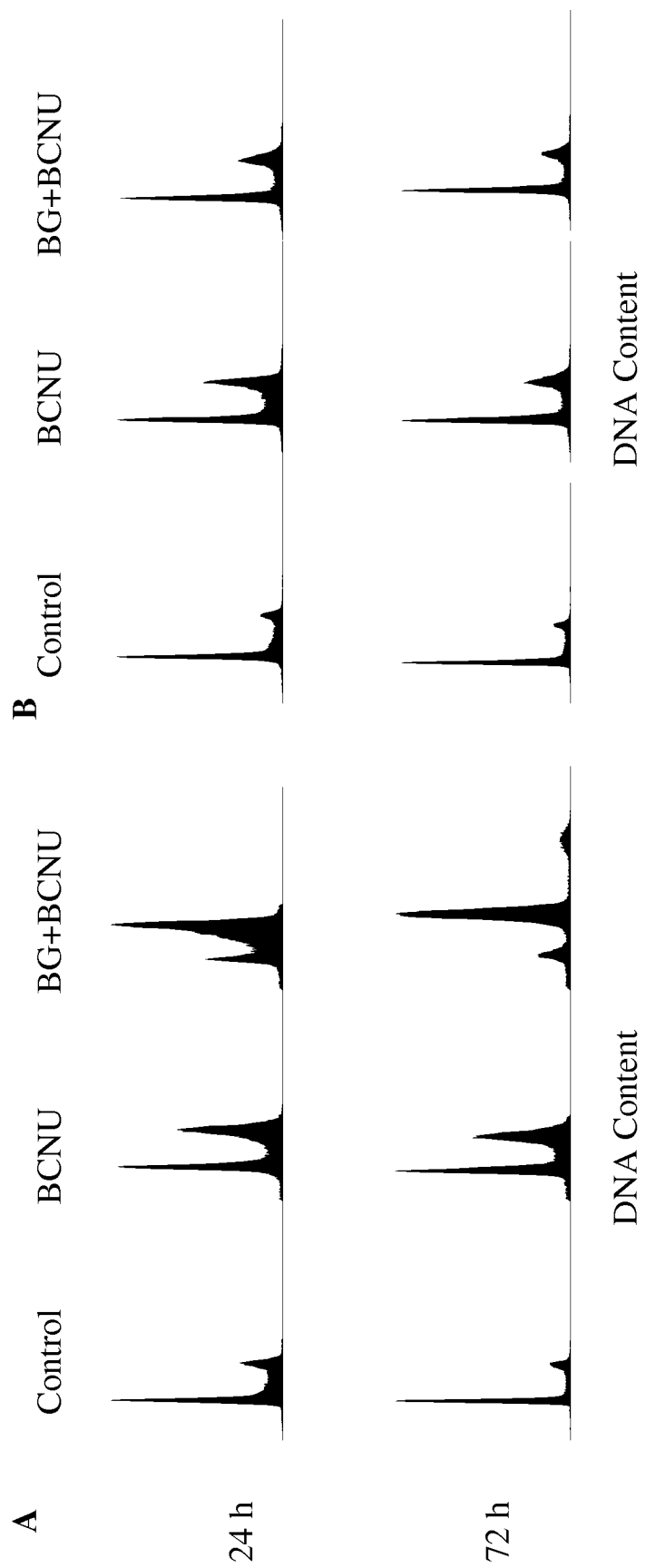
FIG. 7 illustrates cells expressing wild-type MGMT permanently arrest in G2/M after treatment with BG plus BCNU. Cell cycle distribution of HCT116 (a) and HCT116 BBR (K165E MGMT) cells (b) after exposure to BCNU (50 μM) alone or BG (50 μM) plus BCNU (50 μM).

After treatment with BCNU alone (50 µM), a similar cell cycle regulation was noted in these two cell lines, in which ~20% of cells underwent growth arrest in the G2/M transition at 24 h and then progressed through the transition to the next cell cycle (FIG. 7A-B). However, the combination of BG with BCNU induced ~80% of HCT116 cells to arrest in G2/M at 24 h and this G2/M arrest remained over 72 h (FIG. 7A).

It was evident that a subset of cells exhibited higher DNA contents (>4N) after the majority of cells were arrested in G2/M and that a portion of subG1 cells (15±4.8% at 72 h) subsequently appeared, suggesting that cell death may be related to the status of abnormal sets of chromosomes. In contrast, HCT116 BBR (K165E) cells did not display prolonged G2/M arrest and did not produce significant subG1 cells at tested time points after exposure to BG plus BCNU (FIG. 7B).

Figure 8:
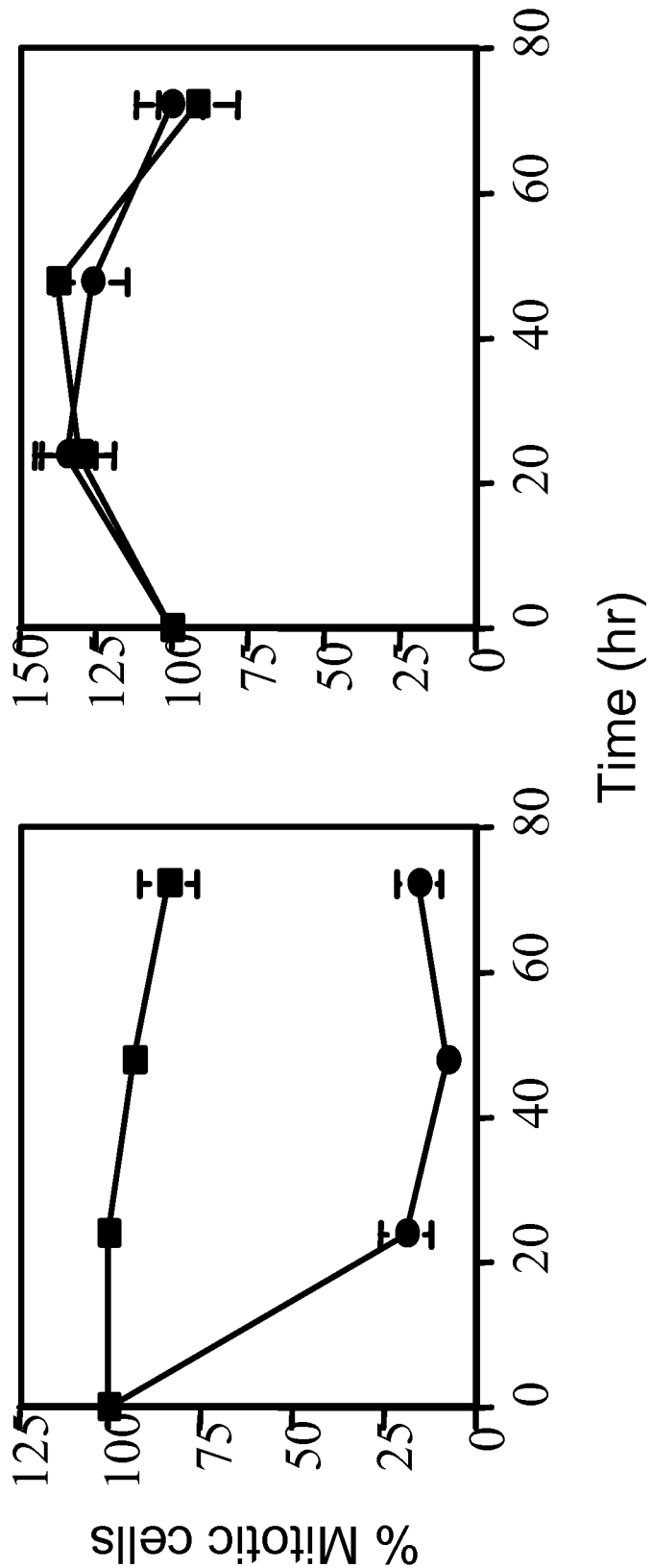
FIG. 8 illustrates a comparison of % mitotic cells after treatments with BCNU alone or BG plus BCNU in HCT116 and HCT116 BBR (K165E) cells.

We used phospho-histone H3, a marker of mitosis, to determine the effect of BG plus BCNU on progression into mitosis. Mitotic content was quantitated from two-dimensional dot plots of DNA content versus phospho-histone H3 staining by flow cytometry (not shown). In these experiments, the percentage of mitotic cells was measured relative to that detected in cells without treatment. After a 24-h-treatment with BG plus BCNU, HCT116 cells showed a significant reduction of mitotic entry that was dramatically decreased to 19% of control value and the inhibition of the progression into mitosis was maintained up to 72 h, whereas there was no significant change of mitotic entry in the cells exposed to BCNU alone (FIG. 8A). In contrast, HCT116 BBR cells displayed slight increases in mitotic entry at the harvesting times analyzed after BG plus BCNU (FIG. 8B).

Figure 9:
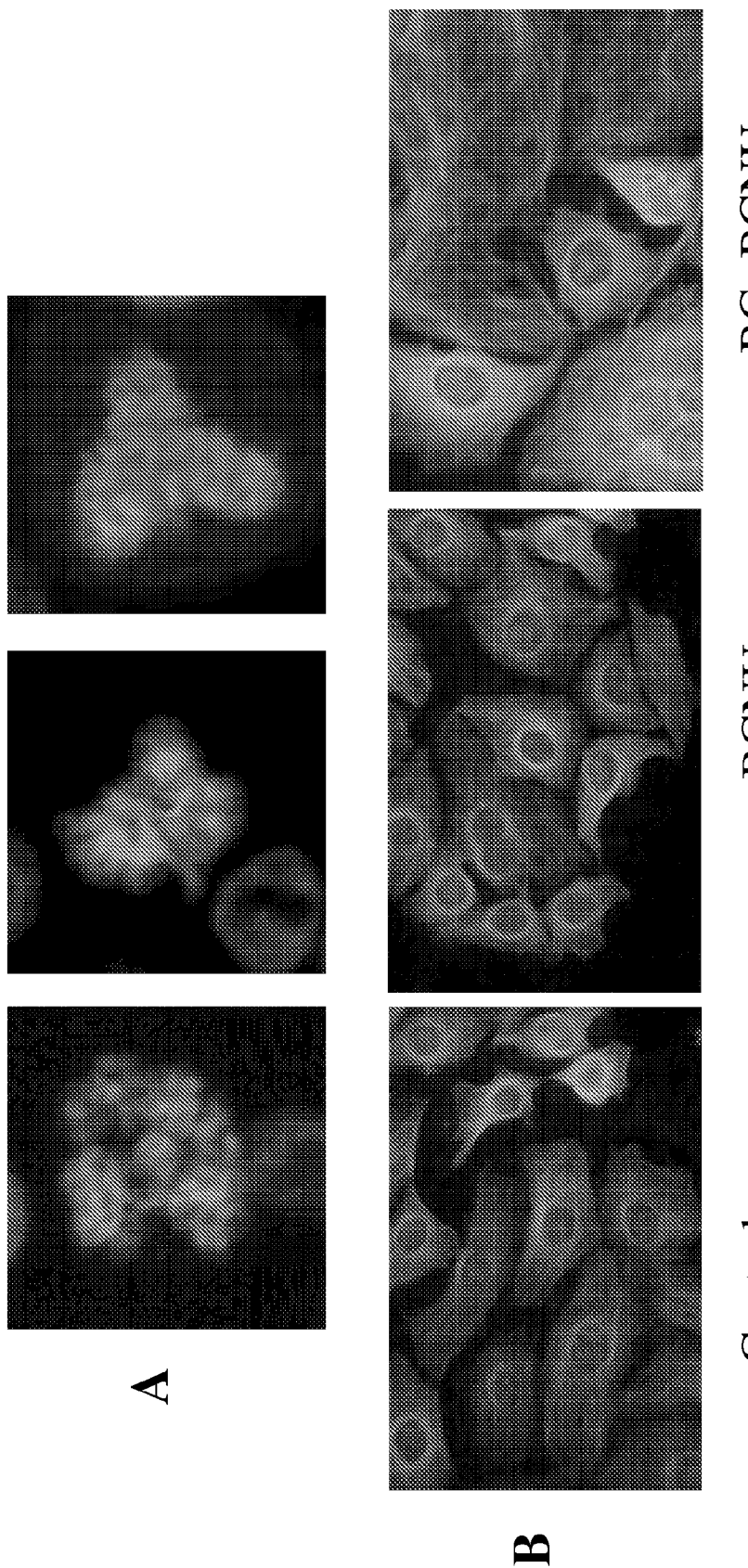
FIG. 9 illustrates high frequencies of mitotic cells with multiple spindle (a), and giant multinucleated cells (b) were observed in HCT116 cells 48 h after exposure to BG plus BCNU.

Mitotic cells stained with anti-phospho-histone H3 antibody revealed that 60% of mitotic cells detected in HCT116 cells treated with BG plus BCNU contained multiple spindle poles (FIG. 9A).

Fluorescent images also demonstrated that in HCT116 cells after exposure to BG and BCNU, there was an increase in the number of multinucleated giant cells, which was correlated with the duration of cells arrested in G2/M in HCT116 cells (FIG. 9B).

We have shown that BG plus BCNU treatments, typical mitotic catastrophe features, including prolonged G2/M arrest, abnormal mitosis and giant nucleated cells were observed in HCT116 (p53 proficient) and HCT15 (p53 deficient) but not in cells expressing BG-resistant MGMT (K165E and K165N MGMT, respectively). And the induction of mitotic catastrophe by BG and BCNU is independent of p53 and is not through Chk1 and Chk2 (DNA damage checkpoint pathway) rather through the inactivation of MGMT in cells with low levels of DNA damage that even not enough to activate apoptotic death.

Figure 10:
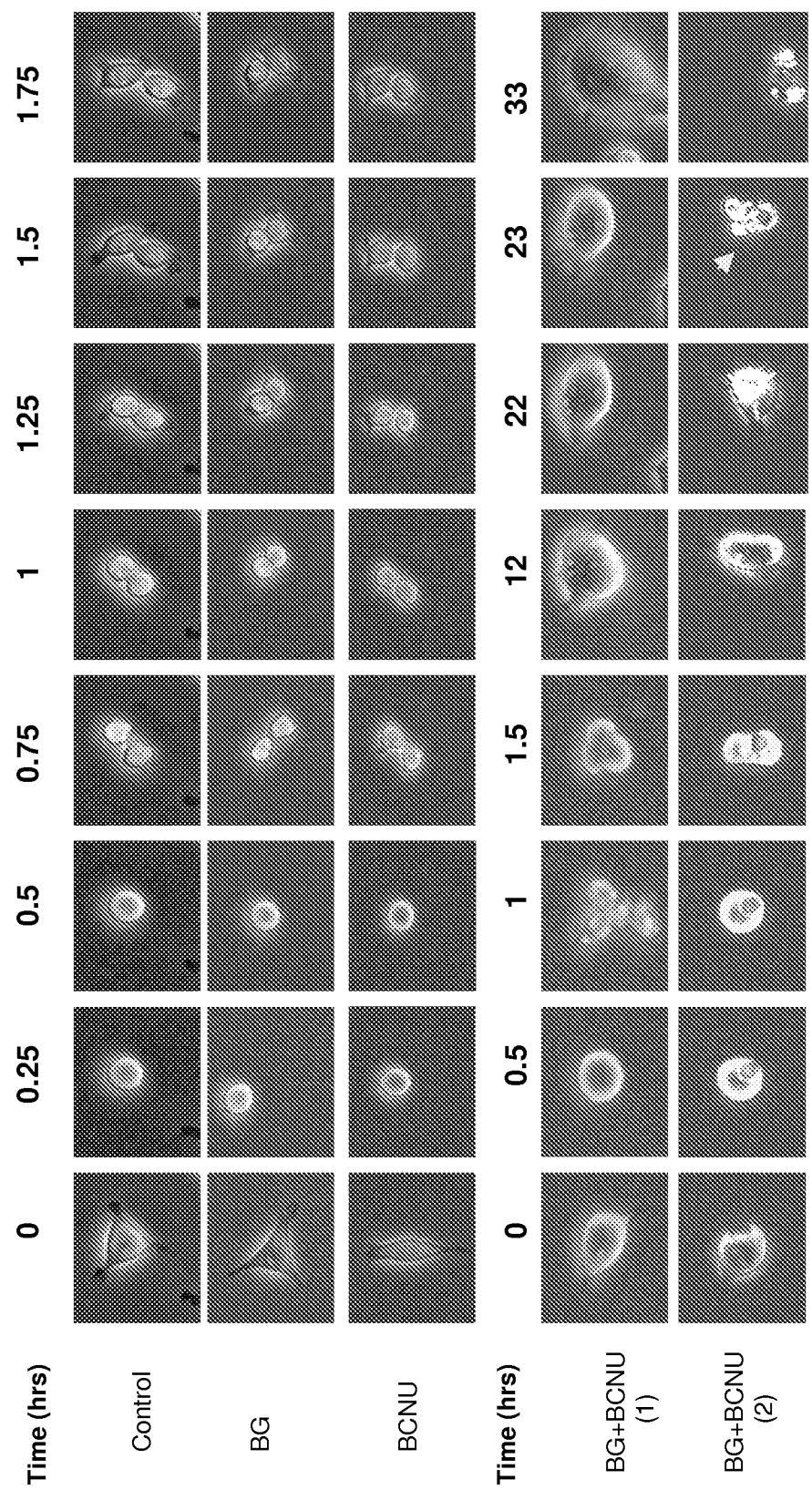
FIG. 10 illustrates time-lapse images (from 0 to 33 hr) in live cells after treatment with different drugs, alone or in combination. The combination of BG and BCNU induced abnormal mitosis with multiple spindle poles (red arrowhead), a failure of cytokinesis (green arrowhead) and mitosis. Cells eventually ended by multinucleated giant cell or mitotic death (yellow arrowhead).

To confirm that inactivation of MGMT affects mitotic progression, cell division processes were monitored using long-term time-lapse imaging in live HCT116 cells after treatments with different drugs or drug combination. Data shown at normal condition, time required for a mitotic cell (the cell becomes round up and shiny) to finishes mitosis (cytokinesis) is about 45-60 min (FIG. 10, control cell panel). The treatment with BG or BCNU alone had no change in this process. However, after BG plus BCNU, cells entered mitosis and arrested in metaphase for more than 20 hr without segregation of chromosomes or underwent abnormal mitosis (with three spindle poles marked by a red arrow head) and cytokinetic abnormalities, resulting in an enlarged cell or died directly from metaphase (marked by yellow arrow head). We proposed that inactivation of MGMT is able to provoke abnormalities in mitotic progression or leads to the defect in mitotic checkpoint, which is a key molecular event to induce mitotic catastrophe when mitotic cells with DNA damage. If it is true, inactivation of MGMT is able to trigger the mitotic death induced by a broad class of DNA damaging agents that generate different distorted DNA structures.

Figure 11:
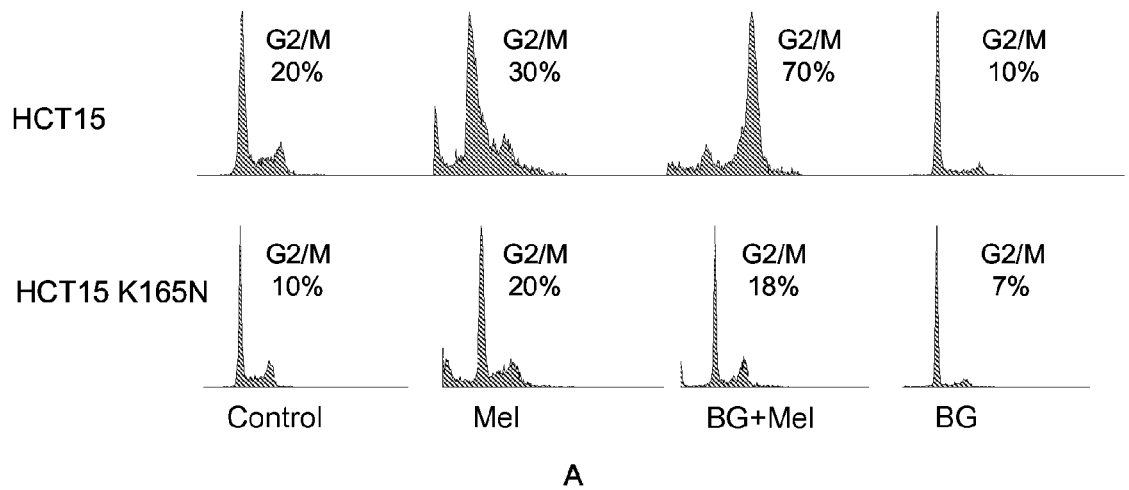
FIG. 11 illustrates mitotic catastrophe triggered by BG-induced inactivation of MGMT in the presence of DNA damage produced by melphalan. A. G2/M arrested by BG+melphalan in HCT15 (wt MGMT). B. multipolar spindle and giant nucleated cells induced by BG+ melphalan. C. BG sensitized toxicity of melphalan is due to mitotic catastrophe resulted from inactivation of MGMT.
Figure 11:
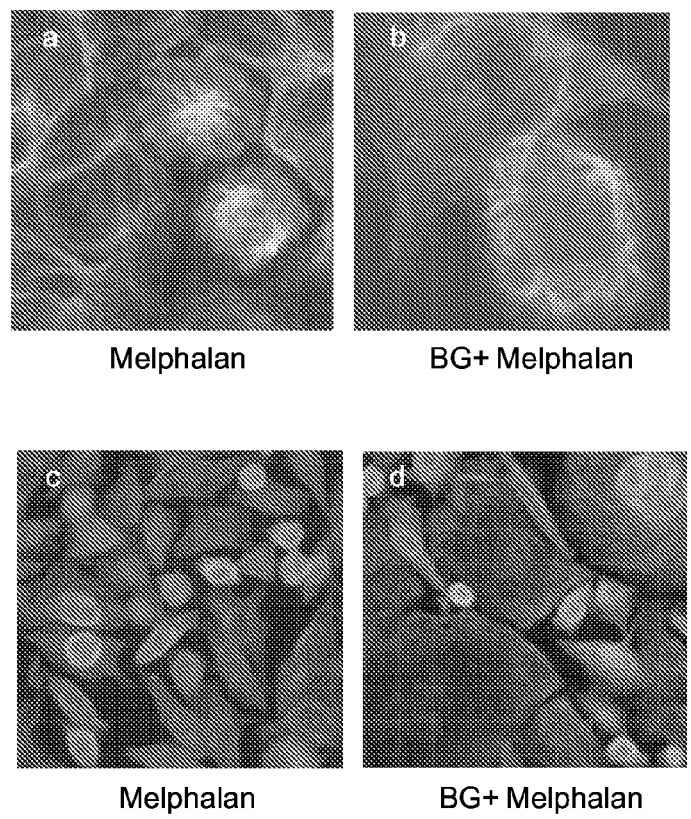
Figure 11:
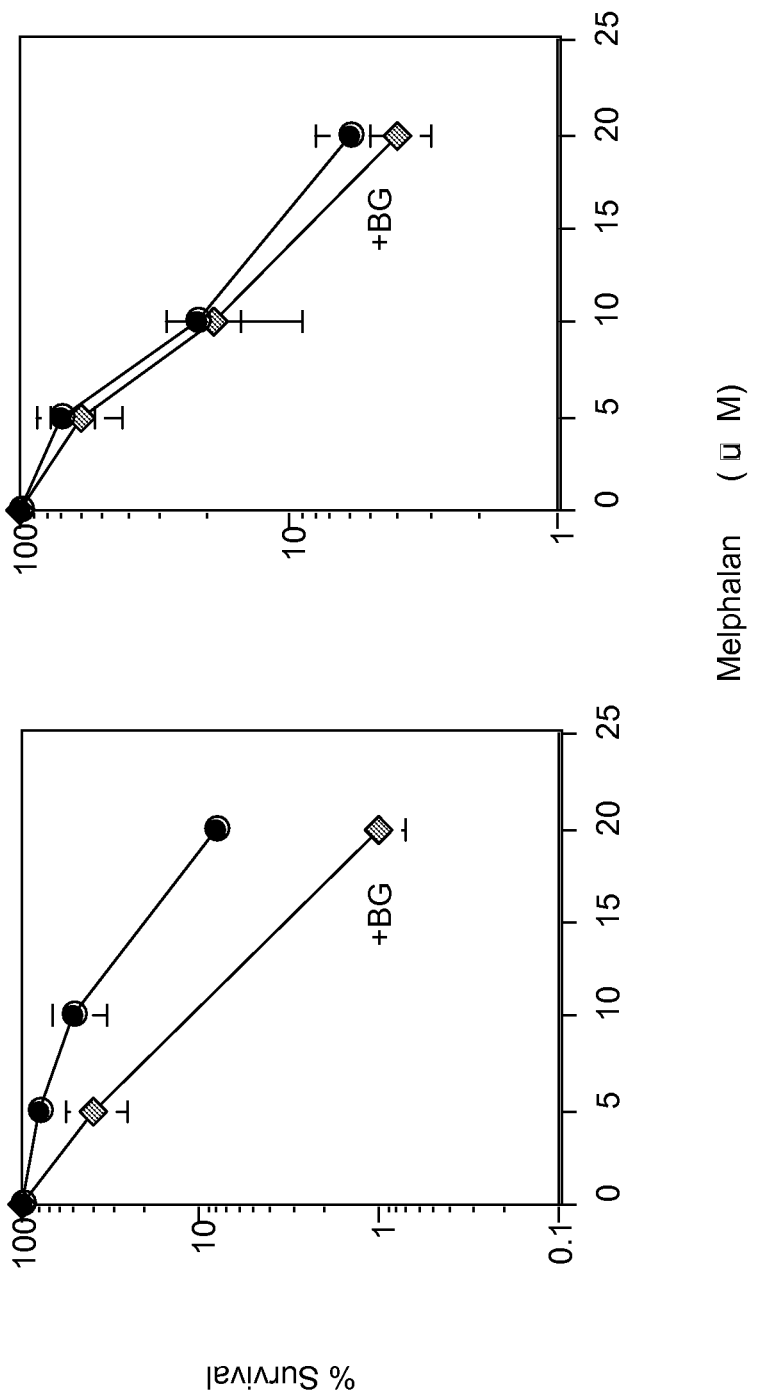

To test our hypothesis that inactivation of MGMT is able to trigger the mitotic death in cells with any type of DNA damage, we treated another paired cell lines, HCT15 (expressing wild type MGMT) and HCT15 K165N (expressing a BG resistant MGMT) with melphalan combined with or without BG. Here we choose melphalan because the DNA damage-induced by melphalan is not associated with the repair capacity of MGMT, allowing us to identify that the mitotic catastrophe-induced by the treatment with BG plus anticancer drug is the results of inactivated MGMT protein initiated the disregulating mitotic progression rather than the results of accumulated DNA lesions due to the depletion of MGMT. Notably, inactivation of MGMT activity in HCT15 cells appeared to arrest cells in a prolonged G2/M following DNA damage (FIG. 11A) and eventually underwent mitotic failure, which was featured by abnormal mitosis with multiple spindles, giant and multinucleated cells (FIG. 11B-D). The observed mitotic catastrophe was associated with the stabilization of phosphorylated Cdc2 (Tyr 15) and CyclinB1 but was independent of the activity of Chk1 and Chk2 (data not shown).

In contrast, no potentiation was observed in HCT15 K165N cells in which K165 N MGMT remains active at the concentrations of BG used in this experiment (FIG. 11C).

Thus, it is apparent that BG enhances the cytotoxicity of melphalan (by 2 fold) through the inactivation of MGMT induced-perturbation of mitotic progression after DNA damage.

Our results have important implications for the use of mitosis-targeted therapeutic strategies that using the combination of a MGMT inhibitor with conventional agents that specifically disrupt mitotic events. This target-based therapy is able to attack and discriminate tumor cells from normal cells. Moreover, our studies also identify that BG-resistant MGMT is able to abolish the mitotic inhibitory effect after DNA damage, suggesting a novel drug-resistant mechanism mediated by MGMT.

Inactivation of MGMT Enhance Therapeutic Efficacy of Taxol in Colon Cancer Tumors, Well Known Taxol Resistant Tumors in Xenograft Setting Athymic mice (5 mice/group) carrying human colon tumors, HCT116/HCT116BBR (K165E MGMT) were treated with BG (30 mg/kg), taxol (15 mg/kg) or BG plus taxol, daily i.p injection for 3 consecutive days. The same treatments were repeated once in the second week.

The experiments were performed to test our hypothesis in vivo that once mitotic checkpoint is impaired through inactivation of MGMT, antimitotic agent, taxol induced mitotic catastrophe can be triggered at lower doses. The potentiation of taxol antitumor effect by BG will be abolished or reduced in tumors expressing mutant MGMT, which is resistant to BG induced inactivation.

Figure 12:
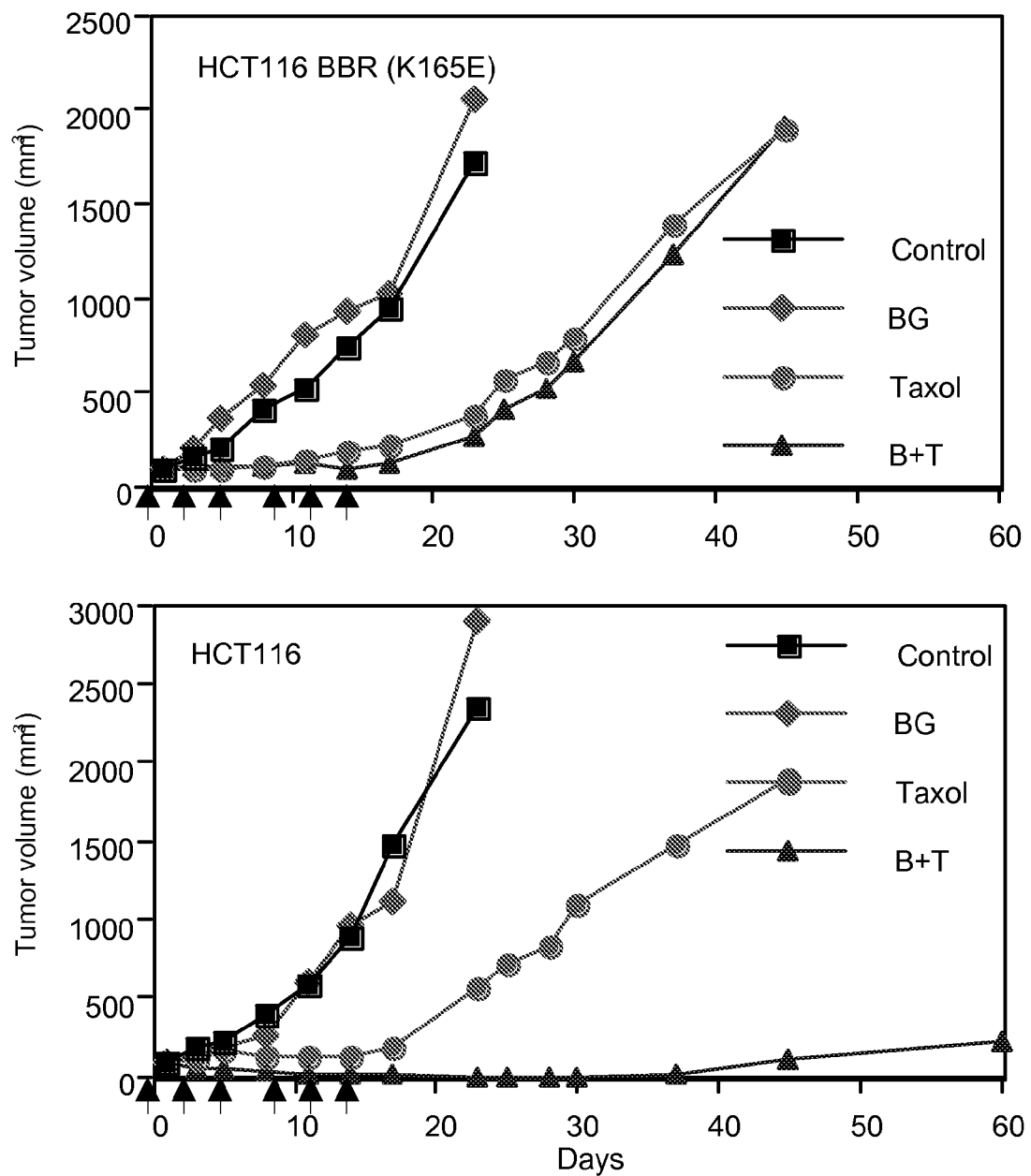
FIG. 12 illustrates BG enhances taxol antitumor effect in HCT116 but not in HCT116 (K165E). B+T: BG plus taxol.

Results (FIG. 12) show that taxol alone has effect on inhibition of tumor growth in both HCT116 and HCT116 BBR (K165E) tumors with tumor growth delays 19.3 and 17.8 days, respectively. ($P<0.05$ versus to control and BG alone groups, two-tailed Student's t test). BG efficiently enhances taxol-antitumor activity, resulting in tumor growth delays over 50 days ($P<0.002$). In contrast, in HCT116 BBR tumors, the combination of BG shows no significant potentiation of taxol. No systematic toxic effects were observed in the studies. These results indicate that the strategy of targeting MGMT to enhance mitotic death in tumor cells is novel and promising.

Inactivation of MGMT Enhance Therapeutic Efficacy of Taxol in Colon Cancer Tumors, Well Known Taxol Resistant Tumors in Xenograft Setting Mice carrying human colon tumors, HCT116 were treated with (A) BG (30 mg/kg), Taxotere (10 mg/kg), or BG plus taxotere, daily i.p injection for 3 consecutive days; and (B) O6-benzyl-oxoguanine (30 mg/kg), Taxol (10 mg/kg), and O6-benzyl-oxoguanine plus Taxol. The same treatments were repeated once in the second week.

Figure 13:
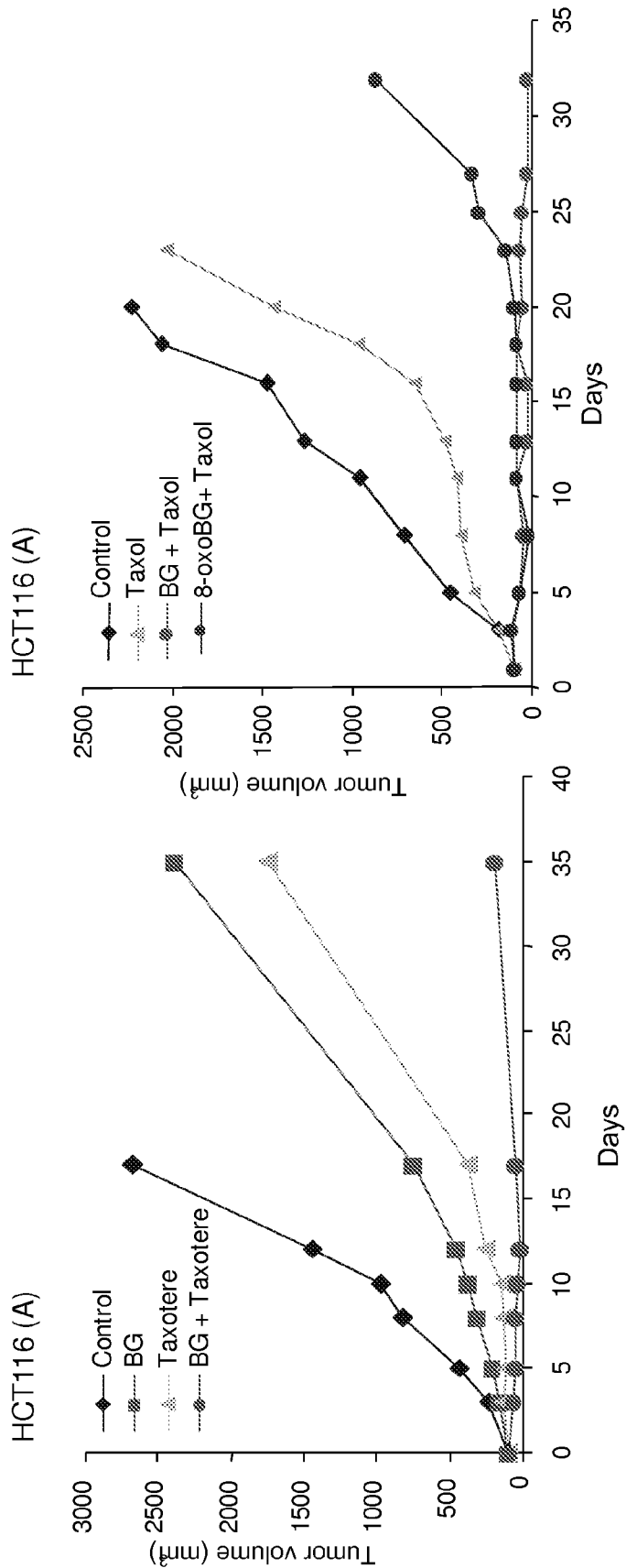
FIG. 13 illustrates (A) the inhibition of tumor growth by the combination of BG (30 mg/kg) and Taxotere (10 mg/kg); and (B) combining taxol with O6-benzyl-oxoguanine (30 mg/kg), an analog of BG enhances anti-tumor activity of Taxol (10 mg/kg).

Results (FIG. 13 A-B) show (A) the inhibition of tumor growth by the combination of BG (30 mg/kg) and Taxotere (10 mg/kg); and (B) combining taxol with O6-benzyl-oxoguanine (30 mg/kg), an analog of BG enhances anti-tumor activity of Taxol (10 mg/kg).

Inactivation of MGMT Enhance Therapeutic Efficacy of Taxol in Human Xenograft Tumors Mice (5 mice/group) carrying breast cancer human xenograft tumors, lung cancer human xenograft tumors (MDA-MB-468), melanoma cancer human xenograft tumors, and lung cancer human xenograft tumors (1975) HCT116 were treated with (A) BG (30 mg/kg), Taxol (10 mg/kg), and BG plus Taxol. The same treatments were repeated once in the second week. The tumor volume v. day were measured.

Figure 14:
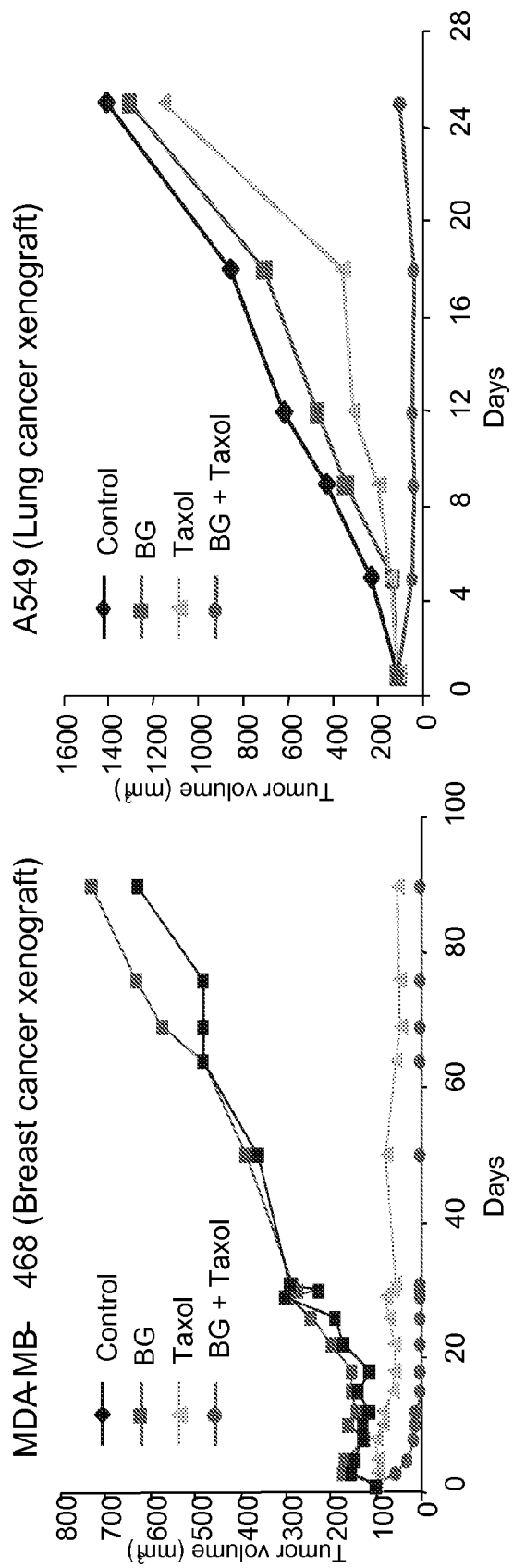
FIG. 14 illustrates the inhibition of tumor growth by combination of BG (30 mg/kg) and Taxol (10 mg/kg) in breast cancer human xenograft tumors and lung cancer human xenograft tumors.

FIG. 14 illustrates the inhibition of tumor growth by combination of BG (30 mg/kg) and Taxol (10 mg/kg) in breast cancer human xenograft tumors and lung cancer human xenograft tumors.

Figure 15:
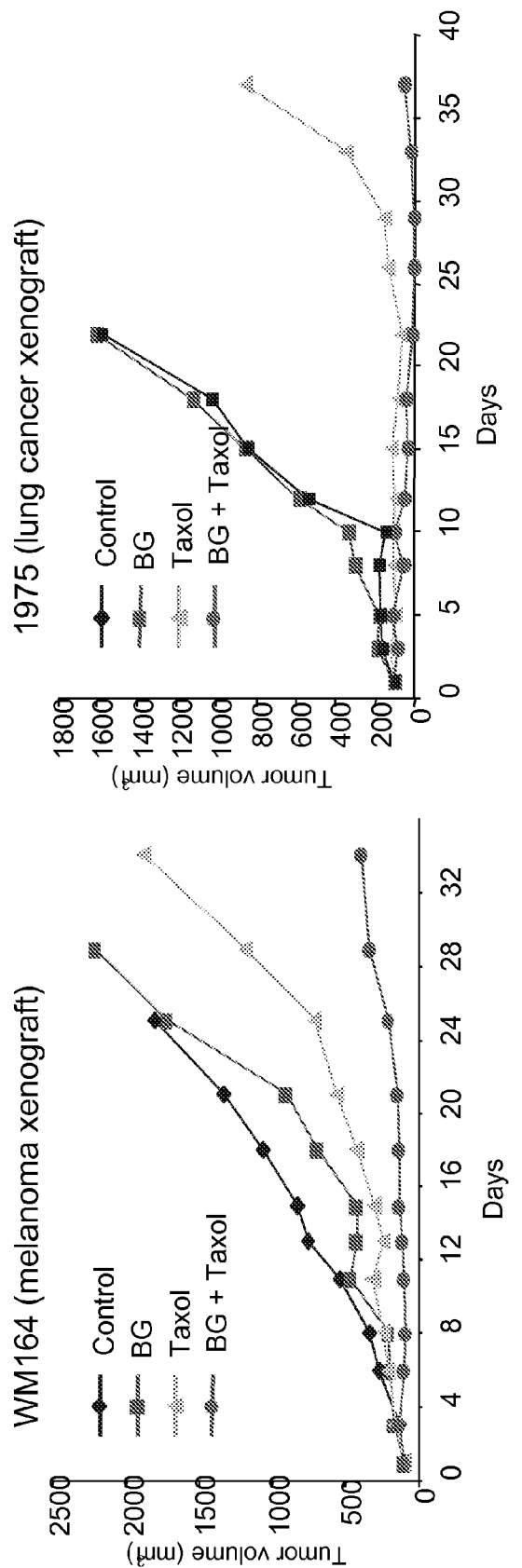
FIG. 15 illustrates the inhibition of tumor growth by combination of BG (30 mg/kg) and Taxol (10 mg/kg) in melanoma human xenograft tumors and lung cancer human xenograft tumors.

FIG. 15 illustrates the inhibition of tumor growth by combination of BG (30 mg/kg) and Taxol (10 mg/kg) in melanoma human xenograft tumors and lung cancer human xenograft tumors.

Research Design and Methods

General Methods: To avoid redundancy, the methods, which are commonly used, are outlined below:

Cell Cycle Distribution and DNA Content Analysis:

The cell cycle distribution and DNA content of cells are determined following fixation of the cells in 90% methanol-PBS at −20° C. after trypsin-mediated detachment from the culture substrate. After permeabilization with 0.2% Triton X-100 and addition of 2 µg/ml DNase-free RNase, the cells are stained with 20 g/ml propidium iodide (PI). Cell cycle histograms are generated from analysis of PI-stained cells by flow cytometry.

Mitotic Cell Determination:

Mitotic cells are quantified via flow cytometric analysis of cells stained positive for the phospho-histone H3. Briefly, cells are harvested, washed with PBS then fixed with 2% paraformaldehyde in PBS, permeabilized for 5 min with 0.05% Triton X-100 in PBS. Fixed cells are then labeled with primary anti-phospho-histone H3 and FITC-conjugated anti-rabbit IgG secondary antibodies (Upstate Bio-technology), followed by staining with PI. Mitotic content is quantitated from two-dimensional dot plots of DNA content versus phosph-histone H3 staining by flow cytometry.

Immunofluorescence and Microscopy:

Cells are fixed for 5 min in methanol at −20° C. or in 4% paraformaldehyde at room temperature for 5 min followed by permeabilization in 0.1% Triton X-100. Fixed cells are incubated for 1 hr at 37° C. with primary antibody, and 30 min at 37° C. with secondary antibody. Fluorochromes (Molecular Probes) are Alexa Fluor 488 (green) and Alexa Fluor 633 (red). Hoechst dye 33258 (Sigma) is used to stain DNA. Images are digitally captured using an Olympus microscope equipped with digital camera.

Western Blot Analysis:

The cells are lysed in lyses buffer (25 mM HEPES, 1.5% Triton X-100, 1% sodium deoxycholate, 0.1% SDS, 0.5 M NaCl, 5 mM NaF, 0.1 mM sodium vanadate, 1 mM phenylmethylsulfonyl fluoride, and 0.1 mg/ml leupeptin at 4° C. with sonication. The proteins in lysates are separated by electrophoresis on a SDS-polyacrylaminde gel. Proteins are transferred to immobilon-P transfer membrane (Millipore Corp) and immunoblotted with appropriate antibodies under conditions recommended by the manufacture. Detection is performed with the enhanced chemiluminescence reagent (NEN life Science Products, MA).

Annexin V Staining:

The presence of apoptotic cells is evaluated by Annexin V staining. After a 48-hour exposure to the drugs, the cells were harvested by incubation with trypsin/EDTA (0.025%/0.01% w/v). After two washes with PBS, the cells were resuspended in 1× binding buffer at a concentration of $1\times10^6$ cells/ml. Cells ($1\times10^5$ cells/100 µl) were exposed at room temperature for 15 minutes to 5 µL Annexin V-PE and 5 µL 7-AAD (BD Bioscience) following the instructions of the manufacturer. Analysis is carried out by FACSort (Becton Dickinson & Co., Mountain View, Calif.).

From the above description of the invention, those skilled in the art will perceive improvements, changes and modifications. Such improvements, changes and modifications within the skill of the art are intended to be covered by the appended claims. All patents, publications, and reference cited in the application are herein incorporated by reference in their entirety.

Having described the invention, the following is claimed:

1. A method of treating a cancer in a subject that is resistant to treatment with an antimitotic agent comprising: administering to the cancer of the subject an MGMT inhibitor and an antimitotic agent; the MGMT inhibitor being administered at an amount effective to potentiate the effect of the antimitotic agent at promoting mitotic cell death of the cancer, wherein the antimitotic agent is a taxane and the MGMT inhibitor is selected from the group consisting of $O^6$-benzylguanine (BG), $O^6$-2-fluoropyridinylmethyl guanine (FPG), $O^6$-3-iodobenzyl guanine, $O^6$-4-bromophenylguanine (PaTrin-2, UK), and $O^6$-5-iodothenylguanine, $O^6$-benzyl-8-oxoguanine (MW 257), $O^6$-(p-chlorobenzyl)guanine, $O^6$-(p-methylbenzyl)guanine (MW255), $O^6$-(p-bromobenzyl)guanine (MW 320), $O^6$-(p-isopropylbenzyl)guanine (MW 283), $O^6$-(3,5-dimethylbenzyl)guanine (MW 269), $O^6$-(p-n-butylbenzyl)guanine (MW 297), $O^6$-(p-hydroxymethybenzyl)guanine (MW271), $O^6$-benzylhypoxanthine, $N^2$-acetyl-$O^6$-benzylguanine (MW 283), $N^2$-acetyl-$O^6$-benzyl-8-oxoguanine (MW 299), 2-amino-6-(p-methyl-benzyl-thio)purine, 2-amino-6-(benzyloxy)-9-[(ethoxycarbonyl)methyl]purine, 2-amino-6-(benzyloxy)-9-(pivaloyloxymethyl)purine, 2-amino-6-(benzyl-thio)purine, O6-benzyl-7,8-dihydro-8-oxoguanine (8-oxo-BG), 2,4,5-triamino-6-benzyloxyprimidine (5-amino-BP), O6-benzyl-9-[(3-oxo-5α-androstan-17β-yloxycarbonyl)methyl]guanine (DHT-BG), O6-benzyl-9-[(3-oxo-4-androsten-17β-yloxycarbonyl)methyl(guanine (AND-BG), 8-amino-O6-benzylguanine (8-amino-BG), C8-linker-glucose-conjugates thereof, 2,4-diamino-6 benzyloxy-5-nitrosopyrimidine (5-nitroso-BP) and 2,4-diamino-6-benzyloxy-5-nitropyrimidine (5-nitro-BP), 2-amino-4-benzyloxy-5-nitropyrimidine, and combinations thereof.

2. The method of claim 1, the antimitotic agent being selected from the group consisting of paclitaxel, docetaxel, and combinations thereof.

3. The method of claim 1, the MGMT inhibitor and the antimitotic agent being administered sequentially.

4. The method of claim 1, the MGMT inhibitor and antimitotic agent being administered orally.

5. The method of claim 1, the MGMT inhibitor and the antimitotic agent being administered intravenously.

6. The method of claim 1, the MGMT inhibitor and the antimitotic agent being administered as a single formulation.

7. The method of claim 1, further comprising administering a DNA damaging agent to the cancer of the subject, wherein the DNA damaging agent comprises at least one of an alkylating agent or ionizing radiation.

8. The method of claim 1, the cancer comprising a solid tumor.

* * * * *